(12) United States Patent
Kraus et al.

(10) Patent No.: US 10,588,536 B2
(45) Date of Patent: Mar. 17, 2020

(54) METHODS AND SYSTEMS FOR IDENTIFYING NON-PENETRATING BRAIN INJURIES

(71) Applicant: NORTHWESTERN UNIVERSITY, Evanston, IL (US)

(72) Inventors: Nina Kraus, Evanston, IL (US); Trent George Nicol, Libertyville, IL (US); Jennifer Lynn Krizman, Glencoe, IL (US); Travis Aaron White-Schwoch, Evanston, IL (US)

(73) Assignee: Northwestern University, Evanston, IL (US)

( * ) Notice: Subject to any disclaimer, the term of this patent is extended or adjusted under 35 U.S.C. 154(b) by 164 days.

(21) Appl. No.: 15/423,910

(22) Filed: Feb. 3, 2017

(65) Prior Publication Data
US 2017/0332935 A1 Nov. 23, 2017

Related U.S. Application Data

(60) Provisional application No. 62/291,206, filed on Feb. 4, 2016.

(51) Int. Cl.
*A61B 5/00* (2006.01)
*A61B 5/0484* (2006.01)
(Continued)

(52) U.S. Cl.
CPC ............ *A61B 5/04845* (2013.01); *A61B 5/00* (2013.01); *A61B 5/0006* (2013.01);
(Continued)

(58) Field of Classification Search
CPC ....... A61B 5/00; A61B 5/0006; A61B 5/0022; A61B 5/04; A61B 5/04004; A61B 5/4064; A61B 8/0808
See application file for complete search history.

(56) References Cited

U.S. PATENT DOCUMENTS

| 8,014,853 B2 | 9/2011 | Kraus |
| 8,712,514 B2 | 4/2014 | Nicol |

(Continued)

FOREIGN PATENT DOCUMENTS

| WO | 2006026548 A1 | 3/2006 |
| WO | 2006122304 A1 | 11/2006 |
| WO | 2014138987 A1 | 9/2014 |

OTHER PUBLICATIONS

Landerl et al., "Predictors of Developmental Dyslexia in European Orthographies with Varying Complexity," Journal of Child Psychology and Psychiatry, vol. 54, No. 6, 2013 (pp. 686-694).
(Continued)

*Primary Examiner* — Max F Hindenburg
(74) *Attorney, Agent, or Firm* — Quarles & Brady LLP; Jonathan Stone

(57) ABSTRACT

The present disclosure provides methods for identifying non-penetrating brain injury in a subject, as well as methods for classifying a subject that received a hit to the body that transmitted an impulsive force to the brain as either having a non-penetrating brain injury or not, by analyzing one or more components of frequency-following response (FFR) following administration of an acoustic stimulus to the subject. In addition, the present disclosure provides methods for assessing a subject's recovery from a non-penetrating brain injury. Also disclosed herein are processes and systems for automatically generating acoustic stimuli and processing brain response data to identify non-penetrating brain injuries in subjects.

33 Claims, 12 Drawing Sheets

(51) Int. Cl.
| | |
|---|---|
| A61B 5/0478 | (2006.01) |
| A61B 5/0482 | (2006.01) |
| A61B 5/04 | (2006.01) |
| A61B 5/0476 | (2006.01) |

(52) U.S. Cl.
CPC .............. *A61B 5/0022* (2013.01); *A61B 5/04* (2013.01); *A61B 5/04012* (2013.01); *A61B 5/0476* (2013.01); *A61B 5/0478* (2013.01); *A61B 5/0482* (2013.01); *A61B 5/0484* (2013.01); *A61B 5/4064* (2013.01)

(56) References Cited

U.S. PATENT DOCUMENTS

| | | | | |
|---|---|---|---|---|
| 8,825,140 | B2 | 9/2014 | Rice | |
| 8,888,712 | B2* | 11/2014 | Turner | A61B 5/04845 600/559 |
| 9,179,854 | B2* | 11/2015 | Doidge | A61B 5/0476 |
| 9,763,571 | B2* | 9/2017 | Kozloski | A61B 3/0025 |
| 9,867,565 | B2* | 1/2018 | Andrews | A61B 5/4064 |
| 10,028,694 | B2* | 7/2018 | Jones | A61B 5/4076 |
| 10,045,730 | B2* | 8/2018 | Fine | A61B 5/4064 |
| 10,165,979 | B2* | 1/2019 | Kozloski | A61B 5/6803 |
| 10,176,578 | B2* | 1/2019 | Puybasset | A61B 5/7264 |
| 2009/0076407 | A1 | 3/2009 | John | |
| 2011/0224570 | A1 | 9/2011 | Causevic | |
| 2011/0295166 | A1 | 12/2011 | Dalton | |
| 2012/0197153 | A1 | 8/2012 | Kraus | |
| 2016/0217267 | A1 | 7/2016 | Kraus | |

OTHER PUBLICATIONS

Langlois, J. A, et al. The epidemiology and impact of traumatic brain injury: a brief overview. J Head Trauma Rehabil. 21, 375-378 (2006).
Lehongre et al., "Altered Low-Gamma Sampling in Auditory Cortex Accounts for the Three Main Facets of Dyslexia," Neuron, vol. 72, Dec. 22, 2011 (pp. 1080-1090).
Leppanen et al., "Infant Brain Responses Associated with Related-Related Skills Before School and at School Age," Clinical Neurophysiology, vol. 42, 2011 (pp. 35-41).
McBride-Chang et al., "Cross-Cultural Similarities in the Predictors of Reading Acquisition," Child Development, vol. 73, No. 5, Sep./Oct. 2002 (pp. 1392-1407).
McKee, A. C. et al. Chronic traumatic encephalopathy in athletes: progressive tauopathy following repetitive head injury. J. Neuropathol. Exp. Neurol. 68, 709 (2009).
Munjal, S. K., et al. Audiological deficits after closed head injury. J. Trauma Acute Care Surg. 68, 13-18 (2010).
Nagarajan et al., "Cortical Auditory Signal Processing in Poor Readers," Proceedings of the National Academy of Sciences, vol. 96, May 1999 (pp. 6483-6488).
Norton et al., "Rapid Automatized Naming (RAN) and Reading Fluency: Implications for Understanding and Treatment of Reading Disabilities," Annual Review of Psychology, vol. 63, 2012 (pp. 427-452).
Olivera, A. et al. Peripheral total tau in military personnel who sustain traumatic brain injuries during deployment. JAMA Neurol. 72, 1109-1116 (2015).
Olulade et al., "Abnormal Visual Motion Processing is not a Cause of Dyslexia," Neuron, vol. 79, Jul. 10, 2013 (pp. 180-190).
Papadimitriou et al., "Which Specific Skill developing During Preschool Years Predict the Reading Performance in the First and Second Grade of Primary School?" Early Child Developmental Care, 2014 (18 pages).
Pegado et al., "Timing the Impact of Literacy on Visual Processing," Proceedings of the National Academy of Sciences, Early Edition, Nov. 2014 (11 pages).

Platt et al., "Embryonic Disruption of the Candidate Dyslexia Susceptibility Gene Homolog KIAA0319-Like Results in Neuronal Migration Disorders," Neurosciences, vol. 248, 2013 (pp. 585-593).
Poeppel, D., "The Analysis of Speech in Different Temporal Integration Windows: Cerebral Lateralization as Asymmetric Sampling in Time,'" Speech Communication, vol. 41, Aug. 2003 (pp. 245-255).
Pruitt, D. et al. Vagus nerve stimulation delivered with motor training enhances recovery of function after traumatic brain injury. J Neurotrauma (2015).
Pugh et al., "Glutamate and Choline Levels Predict Individual Differences in Reading Ability in Emergent Readers," The Journal of Neuroscience, vol. 34, No. 11, Mar. 12, 2014 (pp. 4082-4089).
Pugh et al., "The Relationship Between Phonological and Auditory Processing and Brain Organization in Beginning Readers," Brain and Language, vol. 125, 2013 (pp. 173-183).
Raschle et al., "Altered Neuronal Response During Rapid Auditory Processing and Its Relation to Phonological Processing in Prereading Children at Familial Risk for Dyslexia," Cerebral Cortex, vol. 24, Sep. 2014 (pp. 2489-2501).
Raschle et al., "Functional Characteristics of Developmental Dyslexia in Left-Hemispheric Posterior Brain Regions Predate Reading Onset," Proceedings of the National Academy of Sciences, vol. 109, No. 6, Feb. 7, 2012 (pp. 2156-2161).
Raschle et al., "Structural Brain Alterations Associated with Dyslexia Predate Reading Onset," Neuroimage, vol. 57, 2011 (pp. 742-749).
Russo, N., et al. "Brainstem responses to speech syllables." Clinical Neurophysiology 115.9 (2004):2021-2030.
Saygin et al., "Tracking the Roots of Reading Ability: White Matter Volume and Integrity Correlate with Phonological Awareness in Prereading and Early-Reading Kindergarten Children," The Journal of Neuroscience, vol. 33, No. 33, Aug. 14, 2013 (pp. 13251-13258).
Schatz, P., et al. Sensitivity and specificity of the ImPACT Test Battery for concussion in athletes. Arch. Clin. Neuropsychol. 21, 91-99 (2006).
Shaheen, L. A, et al. Towards a diagnosis of cochlear neuropathy with envelope following responses. J Assoc. Res. Otolaryngol. 16, 727-745 (2015).
Skoe E, et al. Stability and plasticity of auditory brainstem function across the lifespan. Cereb Cortex. 25, 1415-1426 (2015).
Skoe, E. et al. Auditory brain stem response to complex sounds: A tutorial. Ear Hear. 31, 302-324 (2010).
Song et al., "Test-Retest Reliability of the Speech-Evoked Auditory Brainstem Response," Clinical Neurophysiology, vol. 122, 2011 (pp. 346-355).
Song, J. H., et al. Perception of speech in noise: Neural correlates. J Cogn. Neurosci. 23, 2268-2279 (2011).
Sperling et al., "Deficits in Perceptual Noise Exclusion in Developmental Dyslexia," Nature Neuroscience, vol. 8, No. 7, Jul. 2005 (pp. 862-863).
Sprenger-Charolles et al., "Development of Phonological and Orthographic Processing in Reading Aloud, in Silent Reading, and in Spelling: A Four-Year Longitudinal Study," Journal of Experimental Child Psychology, vol. 84, No. 3, 2003 (pp. 194-217).
Tallal, P., "Auditory Temporal Perception, Phonics, and Reading Disabilities in Children," Brain and Language, vol. 9, 1980 (pp. 182-198).
Torgesen et al., "Preventing Reading Failure in Young Children with Phonological Processing Disabilities: Group and Individual Responses to Instruction," Journal of Educational Psychology, vol. 91, 1999 (27 pages).
Turgeon, C., et al. Auditory processing after sport-related concussions. Ear Hear. 32, 667-670 (2011).
Wehr, M. et al. Balanced inhibition underlies tuning and sharpens spike timing in auditory cortex. Nature 426, 442-446 (2003).
White-Schwoch, T. et al. "Physiologic discrimination of stop consonants relates to phonological skills in pre-readers: a biomarker for subsequent reading ability?." Frontiers in Human Neuroscience 7 (2013): 899.
White-Schwoch, T., et al. "Auditory-neurophysiological responses to speech during early childhood: Effects of background noise." Hearing research 328 (2015): 34-47.

(56) References Cited

OTHER PUBLICATIONS

Wright et al., "Deficits in Auditory Temporal and Spectral Resolution in Language-Impaired Children," Nature, vol. 387, May 1997 (oo.176-178).
Žaric, G., et al. "Reduced neural integration of letters and speech sounds in dyslexic children scales with individual differences in reading fluency." PLoS One 9.10 (2014): e110337.
Zatorre, R. J., et al. Lateralization of phonetic and pitch discrimination in speech processing. Science 256, 846-849 (1992).
Zeng, F.-G., et al. Temporal and speech processing deficits in auditory neuropathy. Neuroreport 10, 3429-3435 (1999).
Ziegler et al., "Speech-Perception-In-Noise Deficits in Dyslexia," Developmental Science, vol. 12, No. 5, 2009 (pp. 732-745).
Ahissar et al., "Auditory Processing Parallels Reading Abilities in Adults," Proceedings of the National Academy of Science, vol. 97, No. 12, Jun. 6, 2000 (pp. 6832-6837).
Ahissar et al., "Dyslexia and the Failure to Form a Perceptual Anchor," Nature Neuroscience, vol. 9, No. 12, Nature Publishings, Dec. 2006 (pp. 1558-1564).
Anderson, S., et al. Neural timing is linked to speech perception in noise. J Neurosci. 30, 4922-4926 (2010).
Bajo, V. M., et al. The descending corticocollicular pathway mediates learning-induced auditory plasticity. Nat. Neurosci. 13, 253-260 (2010).
Banai et al., "Reading and Subcortical Auditory Function," Cerebral Cortex, vol. 19, Nov. 2009 (pp. 2699-2707).
Barr, W. B. et al. Sensitivity and specificity of standardized neurocognitive testing immediately following sports concussion. J. Int. Neuropsychol. Soc. 7, 693-702 (2001).
Benasich et al., "Plasticity in Developing Brain: Active Auditory Exposure Impacts Prelinguistic Acoustic Mapping," The Journal of Neuroscience, vol. 34, No. 40, Oct. 1, 2014 (pp. 13349-13363).
Boets et al., "Intact but Less Accessible Phonetic Representations in adults with Dyslexia," Science, vol. 342, Dec. 6, 2013 (pp. 1251-1254).
Boets, B., "Dyslexia: Reconciling Controversies Within an integrative Developmental Perspective," Trends in Cognitive Sciences, vol. 18, 2014 (pp. 501-503).
Carman, A J. et al. Mind the gaps-Advancing research into short-term and long-term neuropsychological outcomes of youth sports-related concussions. Nat. Rev. Neural. 11, 230-244 (2015).
Caspary et al., "Inhibitory Neurotransmission, Plasticity and Aging in the Mammalian Central Auditory System," The Journal of Experimental Biology, vol. 211, 2008 (pp. 1781-1791).
Castles et al., "Is There a Causal Link from Phonological Awareness to Success in Learning to Read?" Cognition, vol. 91, 2004 (pp. 77-111).
Centanni et al., "Knockdown of the Dyslexia-Associated Gene Kiaa0319 Impairs Temporal Responses to Speech Stimuli in Rat Primary Auditory Cortex," Cerebral Cortex, vol. 24, Jul. 2014 (pp. 1753-1766).
Clark et al., "Neuroanatomical Precursors of Dyslexia Identified from Pre-Reading Through to Age 11," A Journal of Neurology: Brain, vol. 137, 2014 (pp. 3136-3141).
Collins, M. W. et al. Relationship between concussion and neuropsychological performance in college football players. J Am. Med Assoc. 282, 964-970 (1999).
Cunningham et al., "Neurobiologic Responses to Speech in Noise in Children With Learning Problems: Deficits and Strategies for Improvement," Clinical Neurophysiology, vol. 112, 2001 (pp. 758-767).
Dekosky, S. T., et al. Traumatic brain injury-football, warfare, and long-term effects. N Engl. J Med 363, 1293-1296 (2010).
Eisenberg, M. A, et al. Duration and course of post-concussive symptoms. Pediatrics 133, 999-1006 (2014).
Finn et al., "Disruption of Functional Networks in Dyslexia: A Whole-Brain, Data-Driven Analysis of Connectivity," Biological Psychiatry, vol. 76, No. 5, Sep. 1, 2014 (21 pages).
Folmer, R. L., et al. Electrophysiological assessments of cognition and sensory processing in TBI: applications for diagnosis, prognosis and rehabilitation. Int. J. Psychophysiol. 82, 4-15 (2011).

Foorman et al., "The Role of Instruction in Learning to Read: Preventing Reading Failure in At-Risk Children," Journal of Educational Psychology, vol. 90, No. 7, 1998 (pp. 37-55).
Franceschini et al., "A Causal Link Between Visual Spatial Attention and Reading Acquisition," Current Biology, vol. 22, May 8, 2012 (pp. 814-819).
Galaburda et al., "Evidence for Aberrant Auditory Anatomy in Developmental Dyslexia," Proceedings of the National Academy of Sciences, vol. 91, Aug. 1994 (pp. 8010-8013).
Gallun, F. J. et al. Performance on tests of central auditory processing by individuals exposed to high-intensity blasts. J Rehabil. Res. Dev. 49, 1005 (2012).
Gathercole et al., "Working Memory in Children With Reading Disabilities," Journal of Experimental Child Psychology, vol. 93, 2006 (pp. 265-281).
Gosselin, N. et al. Evaluating the cognitive consequences of mild traumatic brain injury and concussion by using electrophysiology. Neurosurg. Focus 33, E7 (2012).
Goswami et al., "Amplitude Envelope Onsets and Developmental Dyslexia: A New Hypothesis," Proceedings of the National Academy of Sciences, vol. 99, No. 16, Aug. 6, 2002 (DD. 10911-10916).
Goswami, U., "A Temporal Sampling Framework for Developmental Dyslexia," Trends in Cognitive Sciences, vol. 15, No. 1, Jan. 2011 (pp. 3-10).
Gray, GW. "Phonemic microtomy: The minimum duration of perceptible speech sounds." Communications Monographs 9.1 (1942): 75-90.
Guttorm et al., "Newborn Event-Related Potentials Predict Poorer Pre-Reading Skills in Children at Risk for Dyslexia," Journal of Learning Disabilities, vol. 43, No. 5, 2010 (pp. 391-401).
Hari et al., "Impaired Processing of Rapid Stimulus Sequences in Dyslexia," Trends in Cognitive Sciences, vol. 5, No. 12, Dec. 2001 (pp. 525-532).
Henry, L. C. et al. Metabolic changes in concussed American football players during the acute and chronic post-injury phases. BMC Neural. 11, 105 (2011).
Hornickel et al., "Unstable Representation of Sound: A Biological Marker of Dyslexia," The Journal of Neuroscience, vol. 33, No. 8, Feb. 20, 2013 (pp. 3500-3504).
International Searching Authority, "International Search Report and Written Opinion," issued in connection with International Patent Application No. PCT /US2016/014050, dated May 6, 2016.
International Searching Authority, International Search Report & Written Opinion for application PCT/US2017/016403, dated Apr. 13, 2017, 12 pages.
Johnson, K. L., et al. "Auditory brainstem correlates of perceptual timing deficits." Journal of Cognitive Neuroscience 19.3 (2007): 376-385.
Johnson, K. L., et al. "Brainstem encoding of voiced consonant-vowel stop syllables." Clinical Neurophysiology 119.11 (2008): 2623-2635.
Jordan, B. D. Neurologic aspects of boxing. Arch. Neural. 44, 453-459 (1987).
Jordan, B. D. The clinical spectrum of sport-related traumatic brain injury. Nat. Rev. Neural. 9, 222-230 (2013).
Joyce, A. S., et al. The Postconcussion Symptom Scale: Utility of a three-factor structure. Med. Sci. Sports Exerc. 47, 1119-1123 (2015).
Kim et al., "Computerized Recognition of Alzheimer Disease-EEG Using Genetic Algorithms and Neural Network," Future Generation Computer Systems, vol. 21, 2005 (pp. 1124-1130).
Kontos, A. P. et al. A revised factor structure for the Post-Concussion Symptom Scale baseline and postconcussion factors. Am. J. Sports Med. 40, 2375-2384 (2012).
Kovelman et al., "Brain Basis of Phonological Awareness for Spoken Language in Children and its Disruption in Dyslexia," Cerebral Cortex, vol. 22, No. 4, Apr. 2012 (pp. 754-764).
Kraus et al., "Auditory Neurophysiologic Responses and Discrimination Deficits in Children With Learning Problems," Science, vol. 273, No. 5277, Aug. 16, 1996 (pp. 971-973).
Kraus, N. et al. Brainstem origins for cortical 'what' and 'where' pathways in the auditory system. Trends Neurosci. 28, 176-181 (2005).

(56) References Cited

OTHER PUBLICATIONS

Kraus, N. et al. Unraveling the biology of auditory learning: A cognitive- sensorimotor-reward framework. Trends Cogn. Sci. 19, 642-654 (2015).
Kraus, N. et al. Consequences of neural asynchrony: a case of auditory neuropathy. J Assoc. Res. Otolaryngol. 1, 33-45 (2000).
Kraus, N., et al. Auditory brain-stem responses in hydrocephalic patients. Electroencephalogr. Clin. Neurophysiol. 59, 310-317 (1984).
Krizman, J., et al. Subcortical encoding of sound is enhanced in bilinguals and relates to executive function advantages. Proc. Natl. Acad Sci. 109,7877-7881 (2012).
Kuhl, P. K., "Early Language Acquisition: Cracking the Speech Code," Nature Reviews: Neuroscience, vol. 5, Nov. 2004 (pp. 831-843).

* cited by examiner

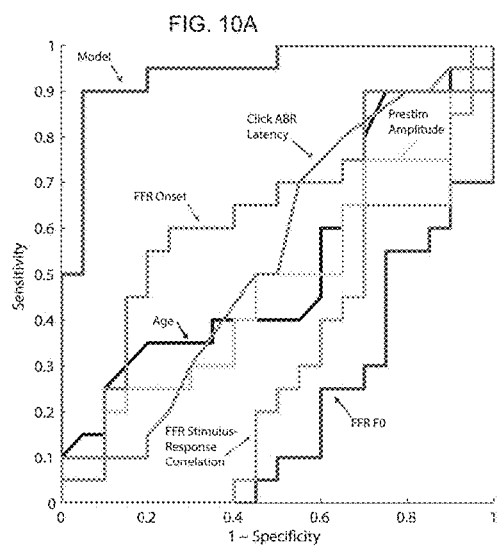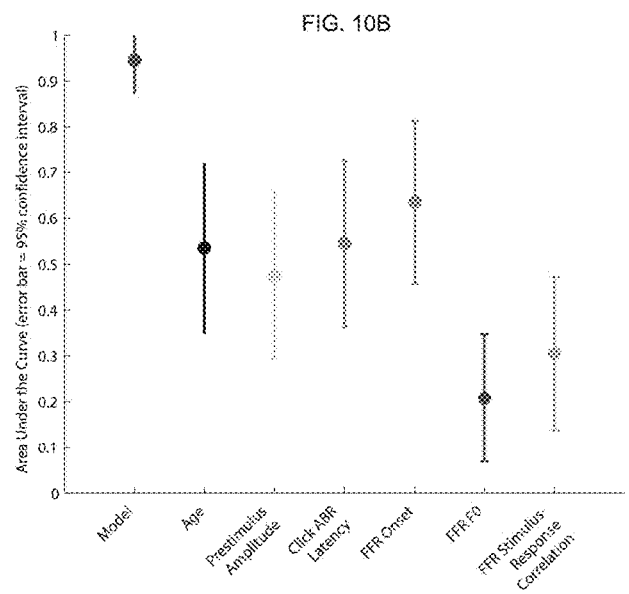

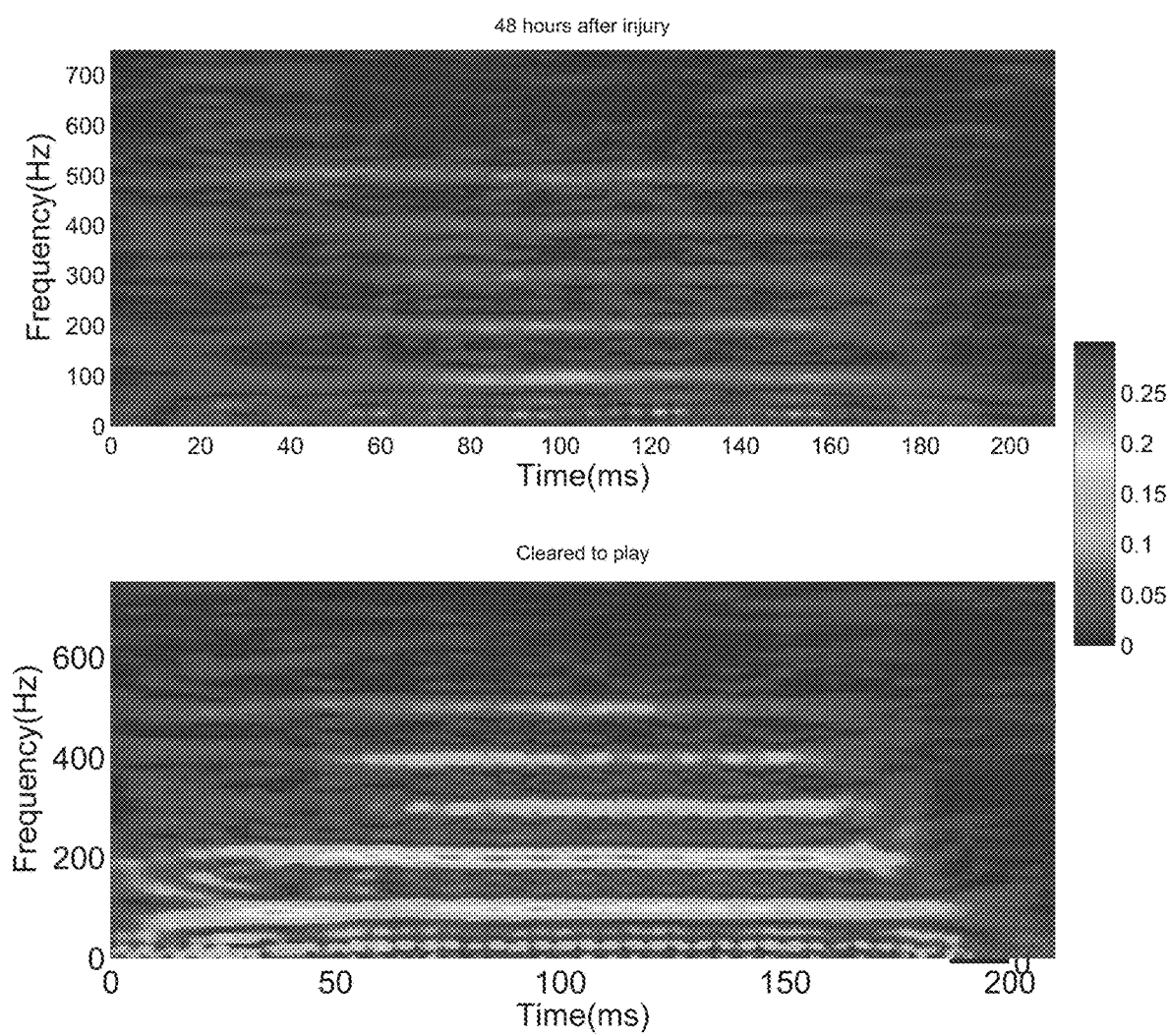

METHODS AND SYSTEMS FOR IDENTIFYING NON-PENETRATING BRAIN INJURIES

CROSS REFERENCE TO RELATED APPLICATIONS

This application claims the priority of U.S. provisional application 62/291,206, filed Feb. 4, 2016, which is hereby incorporated by reference in its entirety.

FIELD OF THE INVENTION

The present disclosure provides methods for identifying non-penetrating brain injury in a subject, as well as methods for classifying a subject that received a hit to the body that transmitted an impulsive force to the brain as either having a non-penetrating brain injury or not, by analyzing one or more components of frequency-following response (FFR) following administration of an acoustic stimulus to the subject. In addition, the present disclosure provides methods for assessing a subject's recovery from a non-penetrating brain injury. Also disclosed herein are processes and systems for automatically generating acoustic stimuli and processing brain response data to identify non-penetrating brain injuries in subjects.

BACKGROUND OF THE INVENTION

Non-penetrating brain injuries carry devastating potential for cognitive, neurologic, and socioemotional disease, but no current approach reliably identifies this type of brain injury or its severity. For example, the current standard for concussion diagnosis is largely subjective in that it relies on accurate symptom reporting by the patient. Thus, there are ongoing efforts to identify objective markers to assist in diagnosing a concussion and predicting recovery.

One area of focus is on cerebrospinal fluid- and blood-based biomarkers that test for sequelae of neural injury. However, these biomarkers are invasive and may not extend to milder forms of non-penetrating brain injury, such as concussions. A second area tries to adopt neuroimaging techniques, such as diffusion tensor imaging and functional magnetic resonance imaging, to detect concussions. However, these approaches rely on expensive equipment and contradictory results are often reported: for example, both increases and decreases in white matter volume have been associated with mild traumatic brain injury. Visual, auditory, and somatosensory evoked potentials have all been explored in individuals following head injury, but contradictory findings have been reported. (Folmer, et al. *Int. J. Psychophysiol.* 82, 4-15 (2011); Munjal, et al. *J. Trauma Acute Care Surg.* 68, 13-18 (2010); Gosselin, N. et al. *Neurosurg. Focus* 33, E7 (2012)) Overall, current neuroimaging and electrophysiological approaches for various forms of non-penetrating brain injury show group differences but overlap between groups potentially thwarts evaluation of individual differences. The limitations of the aforementioned approaches necessitate a fresh methodology that has granularity into the biological minutiae of sound processing, and one that reliably indicates individual differences.

BRIEF DESCRIPTION OF THE FIGURES

FIG. 10A-B depicts graphs showing that the metrics put into the logistic regression model are more accurate identifying groups in aggregate than individually. (A) Receiver operating characteristic (ROC) curves for the model in Example 6 (red) and each of the scores that went into that model. These plots show the tradeoff in sensitivity (true positive rate) and specificity (true negative rate) for each score. For example, as can be seen in the red line a 90% true positive rate for the model corresponds to a 95% true negative rate. Black—subject age in years; Yellow—the amplitude of the prestimulus region of the FFR; Gray—the latency of Wave V of the click-evoked auditory brainstem response; Green—the area of the onset portion of the FFR; Blue—$F_0$ amplitude; Cyan—stimulus-response correlation. (B) Area under the curve (AUC) of each ROC curve are graphed, with colors as described in (A). Higher AUCs correspond to more accurate models. The error bars show the 95% confidence intervals for each of those ROC lines.

FIG. 11 shows a representative subject's FFR 48 hours after sustaining a concussion (top) and after recovery (bottom). This analysis uses the "phase consistency" approach to quantifying the $F_0$. These figures are 3D plots of the FFR. The x-axis is the time point in the response, the y-axis in the frequency point in the response, and the colorscale shows the phase consistency (strength) of each time-frequency point in that plot. Red is the strongest phase consistency and so is best. The $F_0$ of this response is at 100 Hz. After recovery (bottom), when subject was cleared to play, there is a stronger response in that frequency band as compared to 48 hours after sustaining the concussion (top). This figure illustrates (1) using a longer speech stimulus (i.e., 170 msec /da/ syllable) with the phase consistency metric to compute the strength of coding the $F_0$, and (2) following an individual over time and seeing how the response improves through recovery.

SUMMARY OF THE INVENTION

Figure 1:
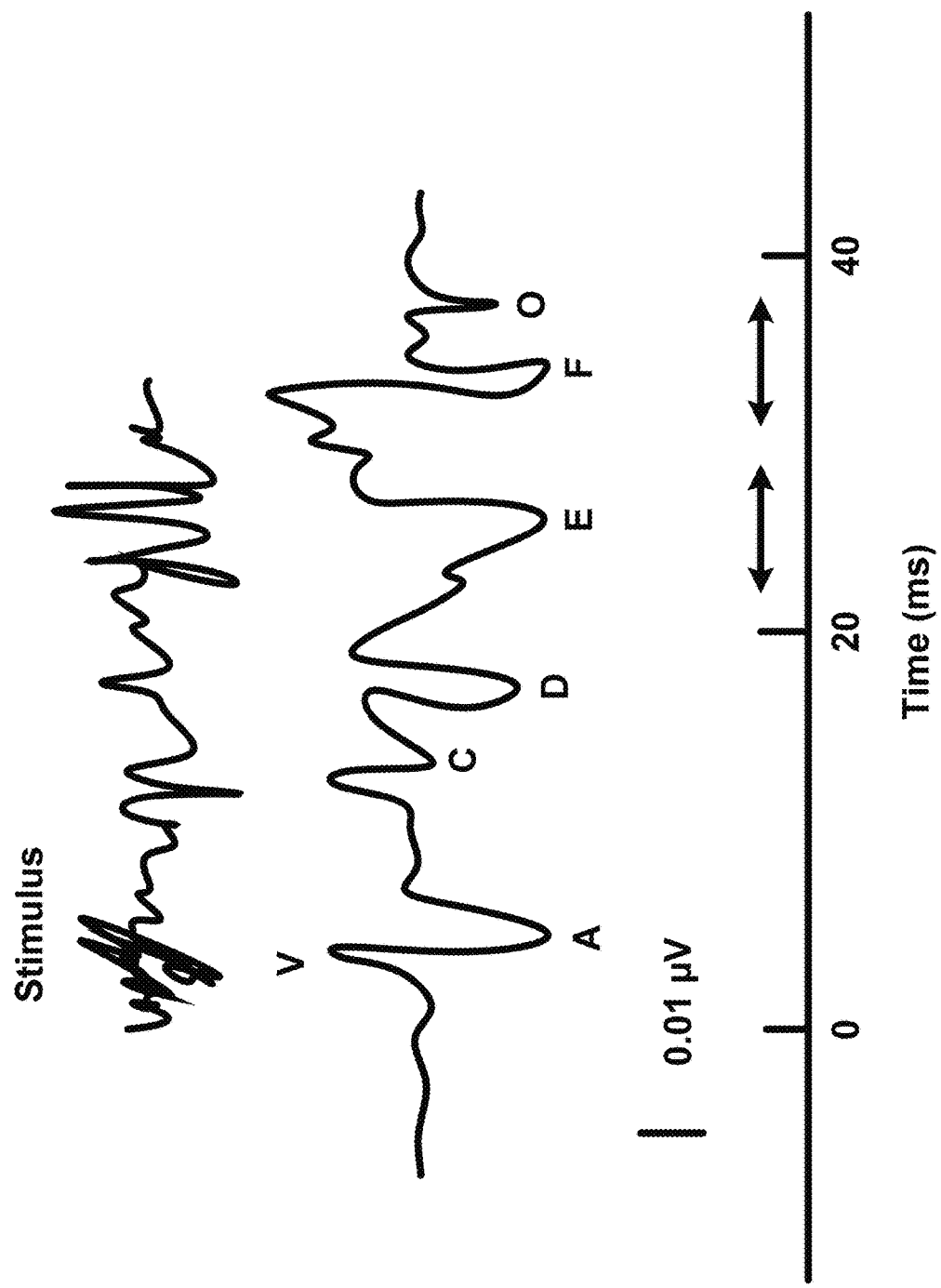
FIG. 1 is a time-domain representation of an acoustic stimulus consisting of a 40 msec /da/ syllable (top) and a brain's response to the stimulus (bottom). The brain response to /da/ includes both transient and sustained response features. The /da/ syllable evokes seven characteristic response peaks that are termed V, A, C, D, E, F, and O. As can be seen in this figure, these peaks relate to major acoustic landmarks in the stimulus. Peaks in the recorded brain response occur 7 to 8 msec after the corresponding stimulus landmark, which is consistent with the neural transmission delay. In this figure, the stimulus waveform is shifted in time to account for this transmission delay and to maximize the visual coherence between the two signals. The V-A complex in the brain response to /da/ is often referred to as the onset response. This sharp onset response arises from the broadband stop burst associated with /d/. Along with V and A, C and O are considered transient responses because they correspond to transient stimulus features, the beginning and end of voicing, respectively. In this figure, the region bounded by D and F forms the frequency following response. Peaks D, E, and F and the small voltage fluctuations between them correspond to sustained stimulus features, namely the fundamental frequency ($F_0$) and its harmonics within the consonant-vowel formant transition. The D-E and E-F interpeak intervals (8 to 9 msec duration, arrows) occur at the period of the $F_0$ of the stimulus, which ramps from 103 to 125 Hz. A systematic approach for identifying these peaks has been established and normative data for 3- to 4-yr olds, 5- to 12-yr olds, and young adults has been published. See, for example, Johnson, et al. (2008), *Clin Neurophysiol,* 119, 2623-2635; or Dhar, S., Abel, R., Hornickel, J., et al. (2009), *Clin Neurophysiol,* 120, 959-966; or Skoe et al. (2014), *Cerebral Cortex,* 25, 1415-1426. Here, the stimulus plot is scaled to match the size of the response. Hence, the microvolt bar refers only to the response.

One aspect of the invention encompasses methods for identifying non-penetrating brain injury in a subject, the method comprising analyzing one or more components of a subject's frequency following response (FFR) to an acoustic stimulus comprising a complex sound; and identifying the subject as having a non-penetrating brain injury when a value for at least one component of the brain response is anomalous. The method may further comprise analyzing one or more transient responses to an acoustic stimulus.

Another aspect of the invention encompasses methods for identifying non-penetrating brain injury in a subject, the method comprising analyzing one or more components of a subject's frequency following response (FFR) to an acoustic stimulus comprising a complex sound, and identifying the subject as having a non-penetrating brain injury when a value for at least one component of the brain response is anomalous, wherein the component(s) are selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. The method may further comprise analyzing one or more transient responses to an acoustic stimulus.

Another aspect of the invention encompasses methods for identifying non-penetrating brain injury in a subject, the method comprising (a) fitting the subject with electrodes to measure voltage potentials generated from the subject's brain; (b) administering to the subject an acoustic stimulus, wherein the acoustic stimulus is comprised of a complex sound, and the complex sound comprises a consonant, a consonant-to-vowel transition, and optionally a vowel; (c) recording voltage potentials from the subject's brain for at least the duration of the acoustic stimulus; (d) analyzing the voltage potentials to determine one or more components of the brain response; and (e) identifying the subject as having a non-penetrating brain injury when a value for at least one component of the brain response is anomalous; wherein the components are selected from the group consisting of fundamental frequency ($F_0$), neural timing of a sustained response peak, response amplitude over a time window that comprises some or all of the consonant-vowel transition, and stimulus-response correlation over a time window that encompasses some or all of the consonant-vowel transition.

Another aspect of the invention encompasses methods for classifying a subject that received a hit to the body that transmitted an impulsive force to the brain as either having a non-penetrating brain injury or not, the method comprising analyzing one or more components of a subject's frequency following response (FFR) to an acoustic stimulus comprising a complex sound; and classifying the subject as having a non-penetrating brain injury when a value for at least one component of the brain response is anomalous. The method may further comprise analyzing one or more transient responses to an acoustic stimulus.

Another aspect of the invention encompasses methods for classifying a subject that received a hit to the body that transmitted an impulsive force to the brain as either having a non-penetrating brain injury or not, the method comprising analyzing one or more components of a subject's frequency following response (FFR) to an acoustic stimulus comprising a complex sound; and classifying the subject as having a non-penetrating brain injury when a value for at least one component of the brain response is anomalous, wherein the component(s) are selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. The method may further comprise analyzing one or more transient responses to an acoustic stimulus.

Another aspect of the invention encompasses methods for classifying a subject that received a hit to the body that transmitted an impulsive force to the brain, the method comprising (a) fitting the subject with electrodes to measure voltage potentials generated from the subject's brain; (b) administering to the subject an acoustic stimulus, wherein the acoustic stimulus is comprised of a complex sound, and the complex sound comprises a consonant, a consonant-to-vowel transition, and optionally a vowel; (c) recording voltage potentials from the subject's brain for at least the duration of the acoustic stimulus; (d) analyzing the voltage potentials to determine one or more components of the brain response; and (e) classifying the subject as having a non-penetrating brain injury when a value for at least one component of the brain response is anomalous; wherein the components are selected from the group consisting of fundamental frequency ($F_0$), neural timing of a sustained response peak, response amplitude over a time window that comprises some or all of a consonant-vowel transition, and stimulus-response correlation over a time window that encompasses some or all of a consonant-vowel transition.

Another aspect of the invention encompasses method for assessing a change in a non-penetrating brain injury, the method comprises (a) analyzing one or more components of a subject's FFR to an acoustic stimulus comprising a complex sound; (b) re-testing the subject's FFR to the acoustic stimulus at a later time; and determining any differences in the one or more components from step (a). If the absolute value of the difference is greater than would be expected by chance, there is a change in the non-penetrating brain injury Another aspect of the invention encompasses methods for assessing a subject's recovery from a non-penetrating brain injury, the method comprising (a) analyzing one or more components of a subject's brain response to an acoustic stimulus comprising a complex sound; (b) re-testing the subject's brain response to the acoustic stimulus at a later time; and determining any differences in the one or more components from step (a); wherein the component(s) is selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. If the absolute value of the difference is greater than would be expected by chance, there is a change in the non-penetrating brain injury. The direction of the change indicates improvement or worsening/deterioration.

Another aspect of the invention encompasses method for assessing a subject's recovery from a non-penetrating brain injury, the method comprises two steps. The first step comprises (a) testing the subject's brain response to an acoustic stimulus by: (i) fitting the subject with electrodes to measure voltage potentials generated from the subject's brain; (ii) administering to the subject an acoustic stimulus, wherein the acoustic stimulus is comprised of a complex sound, and the complex sound comprises a consonant, a consonant-to-vowel transition, and optionally a vowel; (iii) recording voltage potentials from the subject's brain for at least the duration of the acoustic stimulus; (iv) analyzing the voltage potentials to determine one or more components of the brain response; and (v) identifying a value for at least one component of the brain response that is anomalous; wherein the components are selected from the group consisting of fundamental frequency ($F_0$), neural timing of a sustained response peak, response amplitude over a time window that comprises some or all of the consonant-vowel transition, and stimulus-response correlation over a time window that encompasses some or all of the consonant-vowel transition. The second step comprises (b) re-testing the subject's brain response to the acoustic stimulus at a later time by repeating steps a(i) to a(iv), and identifying the value for the one or more components that were anomalous in step (a)(v) ("the re-test value"); and (c) calculating the difference between the re-test value and the anomalous value. The subject is determined to be recovering from the non-penetrating brain injury when there is a change in the re-test value that is greater than would be expected by chance, and the direction of the change indicates an improvement in the component of the brain response. The subject is determined to not be recovering from the non-penetrating brain injury when (a) there is not a change in the re-test value that is greater than would be expected by chance, or (b) when there is a change in the re-test value that is greater than would be expected by chance, and the direction of the change indicates a deterioration in the component of the brain response.

Other features and aspects of the invention are described in more detail herein.

DETAILED DESCRIPTION OF THE INVENTION

Applicants have discovered that non-penetrating brain injury can be identified in a subject by analyzing one or more components of frequency-following response (FFR) following administration of an acoustic stimulus to the subject. The FFR reflects sustained neural activity over a population of neural elements. Various aspects of the FFR as described in further detail below.

As used herein, the term "non-penetrating brain injury" refers to a type of brain injury caused by an indirect or a direct hit to a subject's body that transmits an impulsive force to the subject's brain. The injury may occur after a single blow or after repeated blows. The indirect or direct hit can be to the head, the neck, or elsewhere on the body. Non-limiting examples of indirect hits to the body that may result in non-penetrating brain injury include whiplash, a blast wave from an explosion, or other acceleration or deceleration forces on the body. Non-limiting examples of direct hits to the body that may result in non-penetrating brain injury include head-to-head contact, head-to-other body part (hand, foot, leg, elbow, shoulder, etc.) contact, head-to-ground contact, head-to-object contact (sports equipment (e.g. ball, puck, stick, sword, surfboard, ski, etc.), moving objects, stationary objects, etc.), etc. Various types of "non-penetrating brain injury" include, but are not limited to, concussions and traumatic brain injury (e.g., mild, moderate, severe, etc.). A subject that has a non-penetrating brain injury may or may not have detectable signs of physical brain injury or symptoms commonly associated therewith. The term "non-penetrating brain injury" excludes penetrating brain injuries. A penetrating brain injury is a head injury in which the dura mater is breached. The term "non-penetrating brain injury" also excludes biological insults to the brain, e.g., protein aggregate diseases (e.g., Alzheimer's disease, Parkinson's disease, Huntington's disease, amyotrophic lateral sclerosis, prion diseases, etc.), demyelinating diseases (e.g., Multiple Sclerosis, Devic's disease, Vitamin B12 deficiency, etc.) bacterial infections, encephalitis, tumors, etc.

A subject of this disclosure is a human or an animal. Suitable subjects include a human, a livestock animal, a companion animal, a laboratory animal, and a zoological animal. In a preferred embodiment, a subject is human. Also contemplated are subjects that have an increased risk of non-penetrating brain injury, including, but not limited to, human subjects that are, or were, athletes (amateur or professional), soldiers, victims of physical abuse, involved in a motor vehicle collision, or involved in a bicycle or pedestrian accident, as well as subjects that had a previous non-penetrating brain injury. Methods of this disclosure may not be suitable for subjects with deafness or known neurological conditions which may have an impact on FFR may be excluded (e.g. multiple sclerosis, epilepsy.)

The present disclosure provides methods for identifying non-penetrating brain injury in an asymptomatic or a symptomatic subject, as well as methods for assessing a subject's recovery from a non-penetrating brain injury. Also disclosed herein are processes and systems for automatically generating acoustic stimuli and processing brain response data to identify non-penetrating brain injuries in subjects. Various aspects of this discovery are described in further detail below.

I. Evoking a Brain Response to a Complex Sound

A brain response to sound is evoked by presenting an acoustic stimulus comprising a complex sound to a subject. The brain's response to the acoustic stimulus can be recorded in a number of different ways. In the present disclosure, the brain's response is measured using electrodes that pick up electrical potentials generated by populations of neurons in the brain. An "acoustic stimulus," as used herein, is an input of one or more sounds. A "complex sound" is a sound comprised of two or more frequencies. The term "brain response" refers to a recorded measurement of the voltage potentials from a subject's brain evoked by an acoustic stimulus comprising a complex sound. An acoustic stimulus may be presented once or multiple times. Each presentation of the same acoustic stimulus may be referred to as a "trial." In embodiments where an acoustic stimulus is presented multiple times, the temporal interval between the offset of one stimulus to the onset of another can vary such that there is no amount of time between the stimuli or various amounts of time are included. This interval is referred to as the interstimulus interval. A non-limiting example of a range for an interstimulus interval may be zero msec to about 80 msec. Considerations for choosing an appropriate interstimulus interval are known in the art. See, for example, Skoe et al., *Ear & Hearing*, 2010, 31(3) and the references disclosed therein.

(a) Acoustic Stimulus

An acoustic stimulus comprises a complex sound and, optionally, background noise.

i. Complex Sound

A complex sound is a sound comprised of two or more frequencies. The term complex sound includes amplitude, frequency, or phase modulated waves. An amplitude modulated wave is when the amplitude of a carrier wave, such as a sine wave, is altered by a modulating wave. For example, a 1000 Hz sine wave carrier could be modulated by a 300 Hz sine wave tone. These waves do not have to be tones. Similarly, a wave can also be modulated in frequency or phase. The term "complex sound" excludes simple sounds known in the art including, but not limited to, clicks and sinusoidal tones that are not modified. A complex sound may be natural, synthetic, or a hybrid. Minimally, a complex sound used in the methods of this disclosure should elicit a clear and reproducible brain response in healthy subjects. Synthetic or hybrid sounds are preferred because they offer precise control over the various aspects of sound but well-characterized audio files of natural sounds are suitable as well. Non-limiting examples of complex sounds include vocal sounds, environmental sounds, and musical sounds. Vocal sounds include, but are not limited to, a speech syllable, a word, and a non-speech vocal sound (e.g., a cry, a grunt, an animal sound, etc.). Musical sounds include, but are not limited to a note played by an instrument, a consonant two-note interval played by an instrument, a dissonant two-note interval played by an instrument, and a musical chord. Environmental sounds include, but are not limited to a rainfall sound, an ocean sound, a car horn, a train whistle, etc.

Complex sounds used in the present disclosure have aspects that maximize transient and sustained brain responses. In one aspect, a complex sound has one or more strong transient features. Transient features are brief and nonsustained, and evoke fast response peaks lasting fractions of millisecond (i.e., a transient brain response). The relative strength of a transient feature refers to the timing and/or amplitude. The onset of sound and the offset of sound are common transient features of complex sound. The onset of sound is also referred to as "attack," which is the amount of time taken for the amplitude to reach its maximum level. The offset of sound is also referred to as "release," which is the final reduction in amplitude over time. A transient feature may also be an "amplitude burst," which is an abrupt change in the amplitude envelope of a complex sound. For example, a baby's cry can include multiple amplitude-bursts that produce a series of sharp, transient responses.

For a given group of complex sounds, the strength of a transient feature can be determined by one of skill in the art through routine experimentation, or may be known in the art. For example, among speech sounds, obstruent stop consonants (e.g., /d/, /p/, /k/, /t/, /b/, /g/, etc.) have faster and steeper onsets than affricate consonants (e.g., /tʃ/ and /dʒ/, etc.), which have faster and steeper onsets than fricative consonants (e.g., /z/, etc.), which have faster and steeper onsets than sonorant consonants (e.g. nasals, glides, and slides (e.g., /r/, /l/, etc.). Similarly, musical sounds have varying attack properties that depend on the instrument and how the instrument is played. For example, percussive instruments have fast, steep attacks, and bowed string instruments have comparatively smoother attacks; and a plucked string has a shorter rise time than a bowed string.

In another aspect, a complex sound has a fundamental frequency ($F_0$) in the range of about 50 Hz to about 500 Hz. Fundamental frequencies within this range elicit a strong (i.e., sustained), phase-locked brain response to the $F_0$ and its harmonics. Because phase-locking may become weaker with increasing frequency, a $F_0$ range of about 50 Hz to about 400 Hz may be preferred. Alternatively, the $F_0$ range may be a range about 80 Hz to about 400 Hz, or about 80 Hz to about 300 Hz. In some embodiments, a complex sound may have an $F_0$ that is stable. In some embodiments, a complex sound may have an $F_0$ that changes. In other embodiments, the stimulus may be manipulated to remove the $F_0$ and only contain the harmonic integer frequencies of the $F_0$. In this instance a listener still perceives a fundamental frequency that is approximated as the common denominator from the harmonics. For example, a harmonic series at 200, 300, 400, and 500 Hz would result in a perceived $F_0$ at 100 Hz, and there would be a brain response at 100 Hz.

In embodiments where the complex sound is a speech sound, voiced portion(s) of the sound provide the sustained features. Many, but not all, consonants sounds are unvoiced, meaning that the vocal cords are not in motion. In most languages all vowels are voiced, meaning that the vocal cords are in motion. Thus, a "consonant-to-vowel transition" often involves a change, acoustically, from an unvoiced speech segment to a voiced speech segment. Non-limiting examples of a voiced portion of a sound include a consonant-to-vowel transition, a voiced consonant transition, or a steady-state vowel portion. Though non-speech vocal sounds from animals do not include consonants and vowel, they do contain voiced sounds (for those animals with vocal cords) and other sounds filtered by the vocal tract. As such, non-speech vocal sounds contain acoustic features that are substantially similar to a consonant-to-vowel transition in a speech sound.

The duration of a complex sound can vary. The minimum duration is at least one cycle of the complex sound's $F_0$. For example, the duration may be 1, 2, 3, 4, 5, 6, 7, 8, 9, 10 or more cycles of the complex sound's $F_0$. A skilled artisan can determine an appropriate number of cycles by routine experimentation, or based on teachings in the art. For example, the prior art teaches that musical timbre and vowel identity can be accurately determined from one to four cycles of the $F_0$ but pitch identification typically requires about four or more cycles. See, for example, Gray, G. W. (1942), *Speech Monographs*, 9, 75; or Robinson, K. (1995), *Music Perception*, 13, 1-15; or Robinson, K., & Patterson, R. D. (1995), *J Acoust Soc Am*, 98, 1858-1865. Generally speaking, the only factor limiting the duration of an acoustic stimulus is the feasibility of having a subject remain still for a long time. Thus, duration may need to be restricted to present the desired number of acoustic stimuli in a reasonable amount of time. In various embodiments, the duration may be about 10 msec, about 20 msec, about 30 msec, about 40 msec, about 50 msec, about 60 msec, about 70 msec, about 80 msec, about 90 msec, about 100 msec, or more.

When an acoustic stimulus has a complex sound that is a speech syllable, one strategy to limit duration is to use a consonant and a consonant-vowel (CV) transition without a steady-state vowel. See, for example, Russo et al. (2004), *Clin Neurophysiol*, 115, 2021-2030; Johnson, et al. (2007), *J Cogn Neurosci*, 19, 376-385; Johnson, et al. (2008), *J Neurosci*, 28, 4000-4007; Hornickel, et al. (2009), *Audiol Neurootol*, 14, 198-207; Banai, et al. (2009), *Cereb Cortex*, 19, 2699-2707; Dhar, et al. (2009), *Clin Neurophysiol*, 120, 959-966. Because each consonant-to-vowel transition has a unique formant transition, the steady state vowel can be removed with little impact on the percept. Within this disclosure, speech syllables with a consonant-to-vowel transition are identified by the consonant and the vowel, e.g., /da/, but this nomenclature is understood to include a consonant and a consonant-vowel (CV) transition without a steady-state vowel.

ii. Background Noise

The term "background noise" refers to any sound that occurs at the same time as the sound of interest, e.g., the complex sound intentionally administered to a subject to elicit an auditory response. Non-limiting examples of "background noise" include white noise, pink noise, a murmur of voices, traffic, construction, etc.

iii. Stimulus Creation/Presentation

To elicit a brain response, an acoustic stimulus of the disclosure is created and then presented to a subject. Natural sounds are recorded and then presented, and artificial sounds are synthesized and then presented. Various aspects of presentation including stimulus intensity, monoaural and binaural stimulation, left and right ear stimulation, stimulus polarity, stimulation rate, transducers, jitter in the stimulus presentation, and multiple stimulus conditions are standard in the art. See, for example, Skoe et al., *Ear & Hearing*, 2010, 31(3) and the references disclosed therein. Example description of generating a stimulus can also be found in U.S. Pat. Nos. 8,014,853; 8,712,514; and 8,825,140, and U.S. Ser. No. 15/001,674 co-owned by the present applicant, each of which is herein incorporated by reference in its entirety.

iv. Exemplary Embodiments

In some exemplary embodiments, a complex sound comprises a sound selected from the group consisting of an environmental sound, a musical sound, a speech sound, and a non-speech vocal sound. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec. In certain embodiments, the fundamental frequency ranges from about 130 Hz to about 350 Hz and/or the duration may be at least about 20 msec, at least about 30 msec, or at least about 40 msec. In certain embodiments, the fundamental frequency ranges from about 180 Hz to about 400 Hz and/or the duration may be at least about 20 msec, at least about 30 msec, or at least about 40 msec. In certain embodiments, the fundamental frequency ranges from about 230 Hz to about 450 Hz and/or the duration may be at least about 20 msec, at least about 30 msec, or at least about 40 msec. In certain embodiments, the fundamental frequency ranges from about 280 Hz to about 500 Hz and/or the duration may be at least about 20 msec, at least about 30 msec, or at least about 40 msec.

In other exemplary embodiments, a complex sound comprises a speech sound or a non-speech vocal sound. In other exemplary embodiments, a complex sound consists of a speech sound or a non-speech vocal sound. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec. In certain embodiments, the speech sound is speech syllable, non-limiting examples of suitable speech syllables are listed in the table below.

| Speech Syllable | Examples | Publications |
|---|---|---|
| Vowels | | |
| Synthetic | /a/, /u/ | Krishnan, 2002 |
| Natural | /ɛ/, /i/, /V, /a/, /ae/, /ʌ/, /u/ | Greenburg et al. 1980; Dajani et al. 2005, Aiken & Picton 2006, 2008 |

-continued

| Speech Syllable | Examples | Publications |
|---|---|---|
| Consonant-vowel syllables | | |
| Synthetic | /da/ | Cunningham et al. 2001; Plyler & Ananthanarayan 2001; King et al. 2002; Wible et al. 2004, 2005; Russo et al. 2004, 2005; Kraus & Nicol 2005; Johnson et al. 2007, 2008; Banai et al. 2005, 2009; Burne et al. 2009; Chandarasekaran et al. 2009; Parbery-Clark et al. 2009a |
| | /ba/ | Akhoun et al. 2008a, b |
| | ba-da-ga continuum | Plyer & Ananthanarayan 2001; Johnson et al. 2008; Hornickel et al. 2009b |
| Natural | Mandarin pitch contours | |
| | /yl/ | Krishnan et al. 2005; Xu et al. 2006 |
| | /ml/ | Wong et al. 2008; Song et al. 2008 |
| Hybrid | /ya/ with linearly rising and falling pitch contours | Russo et al. 2008 |

In another exemplary embodiment, a complex sound has a duration of at least about 10 msec and comprises a first sound that transitions directly to a second sound, wherein the first sound has an attack substantially similar to an obstruent consonant and the second sound has a minimum of two formants held steady for one period of $F_0$ and $F_0$ ranges from about 50 Hz to about 500 Hz. In some embodiments the complex sound is a musical sound. In other embodiments the complex sound is an environmental sound. In other embodiments the complex sound is vocal sound.

In another exemplary embodiment, a complex sound comprises a speech syllable, the speech syllable comprising a consonant-vowel transition, a diphthong, a triphthong, or a linguistic pitch contour. The complex sound may or may not be a word. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec.

In another exemplary embodiment, a complex sound consists of a speech syllable, the speech syllable comprising a consonant-vowel transition, a diphthong, or a linguistic pitch contour. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec.

In other exemplary embodiments, a complex sound comprises a consonant, a consonant-to-vowel transition, and optionally a vowel. The complex sound may or may not be a word. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec. Non-limiting examples include /da/, /po/, /chu/, /ki/, /yi/, and /mi/, and variations thereof where the consonants and vowels are substituted for other consonants and vowels that produce similar acoustic features.

In other exemplary embodiments, a complex sound consists of a consonant, a consonant-to-vowel transition, and optionally a vowel. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec. Non-limiting examples include /da/, /po/, /chu/, /ki/, /yi/, and /mi/, and variations thereof where the consonants and vowels are substituted for other consonants and vowels that produce similar acoustic features.

In another exemplary embodiment, a complex sound has a duration of at least about 10 msec and comprises a first sound that transitions directly to a second sound, wherein the first sound is an obstruent consonant and the second sound has a minimum of two formants held steady for one period of $F_0$ and $F_0$ ranges from about 50 Hz to about 500 Hz.

In another exemplary embodiment, a complex sound has a duration of at least about 10 msec and consists of a first sound that transitions directly to a second sound, wherein the first sound is an obstruent consonant and the second sound has a minimum of two formants held steady for one period of $F_0$ and $F_0$ ranges from about 50 Hz to about 500 Hz.

In other exemplary embodiments, a complex sound comprises a consonant, a consonant-to-vowel transition, and optionally a vowel, wherein the consonant is an obstruent stop consonant and the vowel is a low back vowel. A non-limiting example of this complex sound is /da/. The complex sound may or may not be a word. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec.

In other exemplary embodiments, a complex sound consists of a consonant, a consonant-to-vowel transition, and optionally a vowel, wherein the consonant is an obstruent stop consonant and the vowel is a low back vowel. A non-limiting example of this complex sound is /da/. The complex sound has a fundamental frequency ($F_0$) that ranges from about 50 Hz to about 500 Hz, and duration of at least about 10 msec. In certain embodiments, the fundamental frequency ranges from about 80 Hz to about 300 Hz and/or the duration may be at least about 20 msec, at least about 30 msec, or at least about 40 msec.

In other exemplary embodiments, a complex sound comprises a speech syllable selected from the group consisting of /da/, /pa/, /ka/, /ta/, /ba/, and /ga/. The complex sound may or may not be a word. The complex sound has a duration of at least about 10 msec. In certain embodiments, the duration may be at least about 20 msec, at least about 30 msec, or at least about 40 msec.

In other exemplary embodiments, a complex sound consists of a speech syllable selected from the group consisting of /da/, /pa/, /ka/, /ta/, /ba/, and /ga/. The complex sound has a duration of at least about 10 msec. In certain embodiments, the duration may be at least about 20 msec, at least about 30 msec, or at least about 40 msec.

(b) Brain Response

Sound evokes a precise neural response in a subject's brain. In the present disclosure, a brain's response is measured using electrodes that pick up electrical potentials generated by populations of neurons in the brain. The term "brain response" refers to a recorded measurement of the voltage potentials from a subject's brain evoked by an acoustic stimulus comprising a complex sound. Various aspects relating to electrode placement, sampling rate, filtering, signal averaging, and minimizing artifacts can be optimized through routine experimentation. The table below provides a general recommendation for some of these aspects. For further detail, see for example, Skoe et al., *Ear & Hearing,* 2010, 31(3) and the references disclosed therein, as well as U.S. Pat. Nos. 8,014,853; 8,712,514; and 8,825,140, and U.S. Ser. No. 15/001,674, each hereby incorporated by reference in its entirety.

sound. The number and morphology of peaks in a brain response varies based on the complex sound used. All sounds generate a response peak corresponding to the onset of the sound (i.e., an onset peak), though there is typically a lag of about 6 to about 10 msec between when a sound begins and the onset peak. In some instances, a brain response to the onset of sound is a biphasic peak (e.g., positive then negative or negative then positive), rather than a single peak. The positive/negative pair may be referred to as an "onset response." The lag of about 6 to about 10 msec between the onset of sound and an onset peak is referred to as a "neural transmission delay" or a "neural onset delay." An onset peak is a transient response. Additional transient responses may also be present including, but not limited to, a brain response to the onset of an amplitude burst and a brain response to the offset of sound. Complex sounds also generate response peaks that are time-locked to the temporal structure of the eliciting sound. These response peaks are sustained features of a brain response and reflect synchronous, population-wide neural phase locking. Sustained brain

| Parameter | Recommendation | Rationale/Comments |
| --- | --- | --- |
| Electrode placement | Vertical montage (active; Cz; reference; earlobe(s); ground; forehead) | For rostral brain stem recordings; a horizontal montage is used for recording from more peripheral structures |
| Sampling rate | 6000-20000 Hz | Better temporal precision with higher sampling rates |
| Filtering | Low-pass cutoff: 2000-3000 Hz | More defined transient peaks |
|  | High-pass cutoff: 30-100 Hz | Depends on spectral characteristics of stimulus |
|  | If possible, collect cABR with open filters (1-3000 Hz) and band-pass filter off-line using digital filters | Digital filters minimize temporal phase shifts |
| Signal averaging | 2 or more subaverages of 2000-3000 sweeps | Determine response replicability |
|  |  | Spectral-domain averaging will increase spectral estimates and require fewer sweeps |
| Averaging window | Begin 10-50 msec before stimulus onset | An adequate sample of the baseline is needed to determine whether a particular response peak is above the noise floor |
|  |  | For running window analysis, the pre-stimulus time window should be greater than or equal to the duration of the analysis window |
|  | Extend 10-50 msec after stimulus onset | Neural activity should return to baseline |
| Simultaneous cABR-cortical response recording | Only if large files can be accommodated and longer sessions are appropriate |  |
| Minimizing artifacts | Passive collection protocol | Minimizes myogenic artifacts |
|  | Electromagnetic shielded insert ear phones | Minimize stimulus artifact |
|  | Both stimulus polarities | Enables adding of responses to minimize both stimulus artifact and cochlear microphonic |
|  | Use electrically shielded test booth | Minimizes electrical artifact |
|  | Project movie into test booth |  |
|  | Artifact rejection criterion: >20 μV | Exclude trials exceeding typical neural response size; criterion depends on high-pass filter setting | cABRs, auditory brain stem responses to complex sounds.

Generally speaking, a brain response consists of a plurality of positive and negative amplitude deflections, referred to as "response peaks." A brain response is initially recorded as a series of voltages over time (referred to as the time domain response), which can be converted to a series of voltages over frequency by methods well-known in the art (referred to as the frequency, or spectral, domain response). A brain response to complex sound contains multiple, independent, components in both the time domain and the frequency domain. In the context of identifying non-penetrating brain injury, measurements of these components can be meaningful individually or in aggregate.

In the time domain, response peaks are generally classified as either a transient response peak or a sustained response peak. Similarly, regions of the time domain containing transient response peaks or sustained response peaks may be classified as a transient region or a sustained region, respectively. This terminology reflects a brain response to either a transient feature or a sustained feature of a complex responses are often called frequency following responses (FFR). In embodiments where an acoustic stimulus includes an interstimulus interval, the brain response will contain an interstimulus region.

The response peaks for complex sounds routinely used in the art are well-known. For example, a 40 msec /da/ syllable produces six stereotyped peaks: peak V, which is a positive amplitude deflection corresponding to the onset of the stimulus and occurring about 6 msec to about 10 msec after stimulus onset; peak A, which is a negative amplitude deflection immediately following peak A; peaks D, E, and F, which are negative amplitude deflections corresponding to the voicing of the speech sound and occurring at about 22 msec, about 32 msec, and about 42 msec respectively; and peak O, which is a negative amplitude deflection following the offset of the sound, occurring at about 50 msec. A 170 msec /da/ syllable is described in White-Schwoch et al. *Hearing Research* 2015, 325:34-47, and descriptions of /ba/ and /ga/sounds may be found in Johnson et al. *Clinical*

*Neuropsychology* 119:2623-2635. The above description is not limiting. Additional references are known in the art for other complex sounds. If a complex sound is novel, one of skill in the art can characterize the response by methods known in the art.

Neural phase-locking is also evident in the frequency domain, where the brain response follows the periodicity of the eliciting sound. As such, the $F_0$ and harmonics (i.e., integer multiples of $F_0$) of the eliciting sound are reflected in the brain response. Typically all harmonics present in an acoustic stimulus, up to the frequency limits that the brain is able to produce, are present in a brain response. Though, generally speaking, phase locking is more robust when there is less spectral flux (i.e., change in harmonics over time). Non-linearities of the auditory system will often result in additional harmonic peaks in the response beyond those present in the stimulus.

When an acoustic stimulus contains a speech sound or a non-speech vocal sound, certain harmonics are of particular importance phonetically. These harmonics are called "formants." Formants are harmonics that are larger in amplitude than surrounding harmonics (both in the eliciting sound and the response). Each speech sound can be uniquely identified by its characteristic formant pattern, with the first two or three formants being sufficient for identifying most speech sounds. For example, the /a/ sound will typically have a local peak at around 700-750 Hz regardless of the pitch ($F_0$) of the utterance. This is the first formant of /a/. The vowel /i/, on the other hand will have a first formant in the 250-300 Hz range.

In contrast to speech, which is dominated by fast spectrotemporal transitions, music has more prevailing temporal and spectral elements, slower transitions, and finer frequency spacing. In the same way that speech sounds are characterized by unique formant configurations, instruments also have characteristic harmonic structures that impart timbre. Specifically, the timbre of a musical sound is determined by the rise time of the attack, the spectral flux, and the spectral centroid (i.e., the distribution of the harmonics). The clarinet, for example, has a harmonic structure dominated by lower frequency odd harmonics (the even harmonics have been attenuated). The flute, saxophone, trombone, and tuba, which are all characterized by strong odd and even harmonics, can be differentiated by the distribution of the harmonics (e.g., the energy of the tuba is concentrated in the lower harmonics)

The spectral and temporal components of a brain response to complex sound have been described in detail elsewhere, as have methods to measure them. See, for example, Skoe et al., *Ear & Hearing*, 2010, 31(3) and the references disclosed therein. Certain aspects are described below.

i. Brain Response Fundamental Frequency ($F_0$)

One aspect of a brain response to a complex sound is the extent to which the brain response reflects the $F_0$ of the stimulus. As described elsewhere, $F_0$ is a defined parameter based on the acoustics of the eliciting sound. Various aspects of $F_0$ may be analyzed including but not limited to, $F_0$ amplitude, $F_0$ sharpness, $F_0$ phase consistency, or pitch tracking.

To calculate response $F_0$, the time domain response must be converted to a frequency domain response. Suitable methods for achieving this include, but are not limited to, fast Fourier transformation (FFT). FFT may be computed on all or a portion of the time range collected. The time range over which the FFT is calculated may vary provided the range (1) accounts for a neural transmission delay, which is typically about 6-10 msec or may alternatively be determined by the timing of the first amplitude deflection in the brain response; (2) does not extend beyond the end of the brain response, which is typically about 6-10 msec longer than the length of the stimulus plus onset delay, and (3) includes one cycle of the period of the complex sound's $F_0$. For example, at least a 10 msec time period is used to calculate the FFT for a complex sound with an $F_0$ of 100 Hz (period is the inverse of frequency). The FFT may be generated using any standard windowing approach known in the art including, but not limited to, a Hanning window, a Hamming window, a Blackman window, a cosine window, a Nuttall window, a Blackman-Harris window, and a flat-top window, etc. The length of the ramp in computing the FFT can range from 1 msec up to half the length of the time window over which the FFT is calculated. For example, if the FFT is calculated over a 100 msec window, ramp times could include 1 msec, 2 msec, 3 msec, 4 msec, 5 msec . . . up to 50 msec. The arithmetic mean of the amplitude of the spectrum that corresponds to the $F_0$ of the complex sound is calculated.

A response $F_0$ may be then determined by autocorrelation method. An autocorrelation method is a standard procedure that time-shifts a waveform (A) with respect to a copy of itself (A') and correlates A to A' at many such time shifts. For example A(1:10) (i.e., points 1 to 10 of waveform A), is correlated to A'(1:10), then A(1:10) is correlated to A'(2:11), then A'(3:12), etc. The reverse shift also is evaluated, such at A(1:10) is correlated with A'(−1:9) and A'(−2:8) etc. Each time shift is considered a "lag," such that A(1:10) vs A'(1:10) has a lag of 0. A(1:10) vs A'(2:11) has a lag of 1, etc. The fundamental frequency of the waveform A will occur at $1/L_{max}$ Hz, where $L_{max}$ is defined as the lag (in sec) at which the maximum correlation is achieved. The definition of $L_{max}$ is further refined to exclude a lag of 0 which will always be the largest correlation. In practice, if there is a known frequency range of interest, it is possible to restrict the search for the maximum correlation to lags that encompass the range of interest. For example, if a stimulus has a known $F_0$ of 100 Hz, one might wish to restrict the frequency range that is sought in the response to a range of 80 to 120 Hz. In this case, one would only look for the maximal correlation in a lag range of $\frac{1}{80}$ sec to $\frac{1}{120}$ sec (8.33 msec to 12.5 msec). If a peak occurs at a lag of 9.7 msec, one would conclude that the response had an $F_0$ of about 103 Hz. Determining $F_0$ by autocorrelation method is particularly useful when the $F_0$ of the acoustic stimulus or brain response is not known a priori, when the $F_0$ of the acoustic stimulus is known but one desires to determine at what frequency the response occurred, when an acoustic stimulus is missing a fundamental type (e.g. the base frequency), or when a stimulus with a known $F_0$ produces a response peak at a slightly different frequency.

Information known about the stimulus $F_0$ may also be used to choose a suitable frequency window for evaluating one or more aspects of $F_0$. Different frequency regions of the spectrum will be analyzed based on the eliciting sound. In embodiments where the $F_0$ of the complex sound is static, the region may range from one-half the frequency of the eliciting sound $F_0$ (minimum of the region) to twice the frequency of the eliciting sound $F_0$ (maximum of the region). For example, for a complex sound with a 100 Hz $F_0$, the region of interest would be 50-200 Hz. Alternatively, a frequency window as small as 1 Hz may be selected. In embodiments where $F_0$ of the complex sound varied, the parameters for selecting the $F_0$ analyses of the brain response may be determined by the arithmetic mean $F_0$ of the stimulus or the upper and lower bounds. For example, if the complex sound $F_0$ changed from 100-150 Hz the lower bound frequency region of interest could extend as low as 50 Hz and the upper bound as high as 300 Hz.

One aspect of a response $F_0$ is the amplitude. Amplitude may be calculated over a frequency region that is about 1 Hz, or the frequency region may be a range greater than 1 Hz. Methods for calculating response $F_0$ ranges that are greater than one are described above. Any suitable method for quantifying $F_0$ amplitude may be used including, but not limited to the arithmetic mean amplitude over a region, the amplitude at a single frequency point, the total amplitude over a region of interest (summed, integer, root-mean-squared amplitude), and the signal-to-noise ratio of the $F_0$ (i.e., amplitude of $F_0$ vs. amplitude of a neighboring frequency or amplitude of interstimulus region: for example, if $F_0$ is 100 Hz, then a signal-to-noise-ratio may be Amplitude$_{100\ Hz}$/Amplitude$_{90\ Hz}$ or Amplitude$_{100\ Hz}$/Amplitude$_{interstimulus}$). A comparison of the response $F_0$ amplitude to the eliciting sound $F_0$ amplitude (calculated in the same manner) can then be made.

Another aspect of $F_0$ is phase consistency. Phase consistency is a measure of timing variability of individual frequencies in a response. Phase consistency may also be referred to as phase locking or phase-locking factor. Phase consistency may be calculated over a frequency region that is about 1 Hz, or the frequency region may be range greater than 1 Hz. Methods for calculating $F_0$ ranges that are greater than one are described above for both complex sounds with a static $F_0$ and complex sounds where $F_0$ varied.

To calculate phase consistency, first a spectrum is calculated over a discrete time period of the response using a fast Fourier transform, as described above. This results in a vector that contains a length, indicating the encoding strength of each frequency, and a phase, which contains information about the timing of the response to that frequency. To examine the timing variability of the response, each vector is transformed into a unit vector by dividing the FFT by the absolute value of the FFT. This transformation sets the length component of the vector to one, discarding the information about encoding strength but maintaining the phase information. The resultant vector is generated for each response trial and then averaged across trials so that the length of the resulting vector provides a measure of the inter-trial phase consistency. It is acceptable to not use every trial. For example, artifact rejecting, or using other criteria, can result in phase consistency being calculated on a subset of the sweeps. Alternatively, or in addition, some number of trials may be averaged prior to calculating phase consistency (e.g., averaging together every 10 trials), and/or the trials may be first filtered (provided the filters do not exclude the frequency bands of interest). Suitable filters and bandwidths are discussed in section (v). Phase consistency can also be calculated using a bootstrapping method, in which a subset of the trials are selected at random, phase consistency is calculated across that subset of trials, those trials are replaced, and the process is repeated for a given number of times.

Instead of or in addition to determining the phase of the signal at a given time-frequency point, as described above, this approach could be used to extract the frequency of a signal at said point or points. Also, in addition to looking at phase consistency over a single time period in the response, a sliding window analysis can be used to calculate phase consistency over small, overlapping time periods of the response (e.g., a 40 msec window with a 39 msec overlap would result in phase consistency being calculated from 0-40 msec, 1-41 msec, 2-42 msec, etc.).

Other signal processing approaches to determine the instantaneous phase of the signal at specific frequencies are also known in the art including, but not limited to wavelets. Wavelets are convolved with the brain response signal to provide amplitude and phase information for each time-frequency point(s), and then procedures follow as above. These could include Morlet wavelets, Mexican hat wavelets, Meyer wavelets, and more.

Another aspect of a response $F_0$ is the $F_0$ frequency error. The "$F_0$ frequency error" is defined as the difference in frequency (Hz) between the $F_0$ of the complex sound and the maximum spectral peak in the region of interest in the response. For example, if the largest peak of the response from 75-175 Hz was at 125 Hz, and the stimulus $F_0$ was 100 Hz, then the "$F_0$ frequency error" would be +25 Hz.

Another aspect of a response $F_0$ is $F_0$ sharpness. $F_0$ sharpness may also be referred to as $F_0$ bandwidth. To determine $F_0$ sharpness, the $F_0$ peak in the brain response spectrum is identified as detailed above. The width of the corresponding peak is then selected determining the difference between the surrounding ends of that peak a pre-specified amplitude below that peak, such as 3 dB below the peak, 10 dB below the peak, or the entire length below the peak. The frequency difference between these two boundaries are determined and the ratio between the frequency difference and the pre-specified amplitude is determined, called the Q. For example, the Q of a peak at 100 Hz, with the bandwidth 10 dB below it, would be 10 (100/10). Bandwidth may be determined for peaks other than $F_0$, as well.

Another aspect of a response $F_0$ is pitch tracking. Pitch tracking refers to the extent to which a brain response tracks an $F_0$ that changes over time (e.g. a complex sound may have a linear increase in $F_0$ from 100 to 150 Hz over the duration of the sound). The idea is that at any given point in the stimulus, the $F_0$ is at a given instantaneous frequency. As an example, perhaps at time 20 msec the instantaneous frequency is 100 Hz; at 70 msec it is 125 Hz; at 120 msec, it is at 150 Hz. To determine these instantaneous frequencies (either in the stimulus or the response) an autocorrelation approach would be applied to small, overlapping segments of the waveform. For example, to determine the instantaneous frequency at 20 msec, one might extract a segment of the waveform from 0 to 40 msec and apply the autocorrelation technique described above. The resultant derived fundamental frequency ($1/L_{max}$) would be assigned to time 20 msec. Then, one would repeat with a segment of the waveform from 1 to 41 msec. The resultant derived fundamental frequency ($1/L_{max}$) would be assigned to time 21 msec, etc. In this way, a pitch tracking analysis can be achieved, utilizing the "frequency error" method described above. The difference in frequency (Hz) between the $F_0$ of the stimulus and $F_0$ of the response could be computed for each time point, and the absolute values of the resulting frequency errors could be summed to compute an overall frequency error score, where 0 indicates perfect pitch tracking and larger numbers indicate poorer pitch tracking.

ii. Harmonics

Another aspect of a brain response to a complex sound is the extent to which a brain response reflects the harmonics of the stimulus. Various aspects may be analyzed including, but not limited to, harmonic amplitude, phase consistency, spectral flux, and spectral centroid.

Suitable methods for analyzing various aspects of the response harmonics are well-known in the art. These methods include those described for $F_0$, changing parameters as needed to reflect the frequency range of the harmonics. For example, when determining phase consistency of the harmonics, frequency information outside of the $F_0$ is analyzed. This region may be as small as 1 Hz, or it may encompass a range of harmonics. Amplitudes at individual harmonics may also be averaged together. In another example, when creating an average of the response in embodiments where the acoustic stimulus was presented to a subject in multiple polarities (e.g., condensation and rarefaction) then, the responses to one of the polarities can be inverted before averaging (i.e., "subtracted') in order to enhance the response to the harmonics. Alternatively, or in addition, harmonic amplitude may be referenced to the amplitude of a non-stimulus-evoked portion of the response. An example of a non-stimulus-evoked portion of the response would be the interstimulus period, in other words the response to the silence between successive stimulus presentations. This interstimulus-period response would be considered background activity of the brain, and so computing the ratio, for example, $RMS_{harmonic}/RMS_{interstimulus}$ would be considered a signal to noise ratio (SNR).

iii. Neural Timing

Another aspect of a brain response to a complex sound is the speed or timing of one or more response peaks of the brain response. The identity and number of response peaks analyzed can vary depending on the acoustic stimulus. For example, while all complex sounds elicit an onset peak, not all features are shared by every complex sound.

In some embodiments, one or more transient feature is analyzed. In other embodiments one or more sustained feature is evaluated. In other embodiments one or more transient feature and/or one or more sustained feature is evaluated. In each of the above embodiments, as few as one response peak may be analyzed or more than one response peak may be analyzed. When analyzing more than one response peak, the response peaks may or may not be clustered in the same time region.

As a non-limiting example, if the complex sound was /ada/, a subset of peaks in the response time region corresponding to just the /d/ may be analyzed (accounting for the neural onset delay). Alternatively, or in addition, the onset peak could be analyzed and/or the consonant-to-vowel transition (or just a portion thereof) could be analyzed. As another example, when a complex sound has a longer duration and encompasses multiple, discrete features (e.g., complex speech sounds comprising multiple phonemes or syllables or a complex sound that is musical melody or comprised of several musical notes), it might be logical, in these cases, to perform an analysis over discrete acoustic/phonetic portions of the complex sound and response.

Methods for identifying response peaks are well-known in the art, aspects of which are briefly described below. See, for example, Skoe et al., *Ear & Hearing*, 2010, 31(3) and the references disclosed therein.

In one approach, the locations of the stereotyped peaks in a brain response may be determined by the individual who collected the data. The method typically involves the use of two or more subaverages generated by a computer to identify where the peaks in a subject's brain response reliably occur. The peaks are then marked on the final averaged waveform. Alternatively, a normative database may be used in addition to or instead of subaverages. For example, a table listing expected peaks and typical latency ranges for each peak could be consulted. In additional examples, a "norm" response that is the average of all of the individuals in a normative database could be used, or a subject's previous response that already has marked peaks could be used. In yet another example, an algorithm may be used to identify local minima and maxima within a predetermined window. For example, a computer could detect the timing of the largest amplitude point within a pre-specified window (e.g., about 6 to 10 msec for an onset peak). A computer program could use other signal processing approaches to identify these peaks, such as a principal components analysis to identify a peak-to-trough complex in the response. Using the /da/ syllable for illustration, a computer program could identify V and A based on their shape and statistical modeling of the response vs. a norm. Alternatively still, a hybrid method of the above approaches may be used. For example, an algorithm may initially identify peaks and an individual adjusts them, or vice-versa.

An alternative approach to determine neural timing may use a stimulus-response cross-correlation approach, for example as described below. Instead of a correlation value, the timing shift that achieves the maximum correlation is used to quantify neural timing ($L_{max}$=neural timing).

A third approach to determine neural timing may involve calculating the phase delay, also known as the group delay of the response. The group delay calculates the timing of constituent sinusoids in a complex signal, and so provides a frequency-specific measure of timing. It is the rate of change of transmission phase angles of the frequencies in the signal. It is calculated as the negative first derivative of the phase response of a signal:

$$\tau_g(w) = -\frac{d\phi(w)}{dw}$$

where $T_g(w)$ is the group delay, $\phi$ is the phase difference between the signal and response, and w is the frequency. This can be computed across all frequencies ($T_g(w)$)) or for individual frequencies in the response ($T_g(\phi)$). These frequency ranges of interest could be determined based on the criteria discussed under $F_0$ or harmonics.

iv. Response Amplitude

Another aspect of a brain response to a complex sound is the amplitude of one or more response peaks of the brain response. This aspect is conceptually similar to $F_0$ amplitude, however, $F_0$ is a frequency domain measurement and response peaks are time domain measurements. In some embodiments, one or more transient feature is analyzed. In other embodiments one or more sustained feature is evaluated. In other embodiments one or more transient feature and/or one or more sustained feature is evaluated. In each of the above embodiments, as few as one response peak may be analyzed or more than one response peak may be analyzed. When analyzing more than one response peak, the response peaks may or may not be clustered in the same time region.

As a non-limiting example, if the complex sound was /ada/, a subset of peaks in the response time region corresponding to just the /d/ may be analyzed (accounting for the neural onset delay). Alternatively, or in addition, the onset peak could be analyzed and/or the consonant-to-vowel transition (or just a portion thereof) could be analyzed. As another example, when a complex sound has a longer duration and encompasses multiple, discrete features (e.g., complex speech sounds comprising multiple phonemes or syllables or a complex sound that is musical melody or comprised of several musical notes), it might be logical, in these cases, to perform an analysis over discrete acoustic/phonetic portions of the complex sound and response.

Methods for identifying response peaks, and regions of peaks, are discussed above. Computational methods suitable for determining a response amplitude for an individual peak or a region comprising multiple peaks are known in the art and include, but are not limited to, arithmetic mean amplitude over a region, the root-mean-squared [RMS] amplitude of the peak or region, mean amplitude of the points, max point minus min point (i.e., peak-to-peak maximum), sum of the points in the rectified waveform, amplitude at a single frequency point, the total amplitude over a region of interest (summed, integer, root-mean-squared amplitude), etc.

In certain embodiments, the amplitude of a response peak may be referenced to the amplitude of a non-stimulus-evoked portion of the response. An example of a non-stimulus-evoked portion of the response would be the interstimulus period, in other words the response to the silence between successive stimulus presentations. This interstimulus-period response would be considered background activity of the brain, and so computing the ratio $RMS_{response}/RMS_{interstimulus}$ would be considered a signal to noise ratio (SNR). If desired, an SNR may be expressed in decibels (dB) by taking the 10-base log of the RMS amplitude ratio and multiplying by 20.

A comparison of a response peak amplitude to the eliciting sound response peak amplitude (calculated in the same manner) can then be made.

v. Stimulus-Response Correlation

Another aspect of a brain response to a complex sound is the extent to which the response resembles the evoking sound. Stimulus-response correlations may be performed in the time domain or the frequency domain.

To determine stimulus-response correlation in the time, an acoustic stimulus may be filtered across a bandwidth to match the response and each subject's response may be cross-correlated to the filtered stimulus. Other suitable methods known in the art may also be used.

The type of filter may vary(e.g., Butterworth, Chebyshev, elliptic, Kaiser, etc.), as may the order (e.g., first-order, second-order, etc.) which is also known as the number of poles. The higher the order, the less energy is present outside the specified filter bandwidth.

The bandwidth across which the filter is applied may vary. Generally speaking, an acoustic stimulus will have higher frequency content than a frequency following response (FFR) from the brain. Therefore, low-pass filtering of the acoustic stimulus will result in a stimulus waveform that correlates better with the FFR. To select the low-pass filter cutoff, one approach is to match the bandwidth to that of the FFR recording's bandwidth. A second approach is to choose a low-pass filter that approaches the actual frequency content of the FFR. This approach might result in a low-pass filter of about 1000 Hz because typically an envelope-dominated FFR will have little energy above 1000 Hz. Likewise, the choice of high-pass filter may be matched to the FFR recording or may some other value that approximates the lowest frequency present in the FFR collection.

The time window selected for performing the cross-correlation may vary. In one approach, when the complex sound is a speech sound, a selected time window may correspond roughly to the fully-voiced portion of the stimulus. For example, the time window described in the examples for the /d/ stimulus omits the unvoiced consonant release and the transient FFR component corresponding to the onset of voicing. Other time windows, encompassing a voiced (i.e. periodic) response waveform might also be selected. For example, longer speech stimuli may encompass multiple phonemes or syllables. It might be logical, in these cases, to perform this analysis over discrete acoustic/phonetic portions of the stimulus and response. For example, just the voiced portion of a consonant transition. Or, just a steady-state vowel portion. Similar concepts apply to other complex sounds.

The cross-correlation function is a standard procedure that time-shifts one waveform (A) with respect to another (B) and correlates A to B at many such time shifts. For example A(1:10) (i.e., points 1 to 10 of waveform A) is correlated to B(1:10), then A(1:10) is correlated to B(2:11), then B(3:12), etc. The reverse shift also is evaluated, such at A(1:10) is correlated with B(−1:9) and B(−2:8) etc. Each time shift is considered a "lag," such that A(1:10) vs B(1:10) has a lag of 0. A(1:10) vs B(2:11) has a lag of 1, etc. Pearson product-moment correlation, point-biserial, or Spearman techniques may be used to create a correlation score. For example, the Pearson product-moment correlation produces an "r" score. This results in a value scaled from −1 to +1, with +1 meaning perfect correlation, −1 meaning perfect anti-correlation (i.e., identical, but fully out-of-phase), and 0 meaning complete lack of correlation. A type of correlation that produces values outside the −1 to +1 range might also be used.

In performing the cross-correlation, the time-shift (lag) which produces the maximum Pearson's r value (or value produced by another method) is sought. However, there are logical constraints to the lag. For example, it is illogical that the brain response would occur before the stimulus. Therefore, negative lag values are not considered. Likewise, it is known that it takes about 6-10 msec for the auditory pathway to respond to a sound and to propagate the signal to the recording electrodes. Therefore a lag smaller than about 6 msec would likewise be illogical because it is simply not biologically possible. It is also known that it typically does not take longer than about 10-12 msec for a signal to arise. So, an "appropriate lag" is typically a range of about 6 to about 15 msec, or about 6 to about 12 msec. A slightly different lag would also be acceptable.

When performing parametric statistical analysis on Pearson's correlation data, it is a routine procedure to calculate a Fisher-transformed z score. While not strictly necessary, statistical conclusions drawn from non-transformed data may be suspect. This is a mathematical, natural-log-based, transformation that normalizes the r distribution so that all delta-r values, along the −1 to +1 range are equivalently constant. That is, the variance of untransformed r-values that are toward the ends of the range (near −1 or near +1) is much smaller than the variance of r-values at the middle of the range (near 0).

All descriptions and alternatives described above involve time-domain comparisons between an acoustic stimulus and its evoked response. Correlations could also be performed between frequency-domain waveforms of the stimulus and response. The major difference, aside from the frequency-domain conversion itself, is that the allowance for the lag would have to be made in the time domain prior to frequency-domain conversion and a straight (i.e., non-cross-) correlation would be performed. For example, let's say one was interested in a frequency-domain correlation of neural activity to the 20 to 80 msec portion of a particular stimulus. If a typical response, due neural propagation time, arises 8 msec after the stimulus, one would perform a frequency-domain conversion of the 20-80 msec segment of the stimulus and of the 28-88 msec segment of the response. Then, once in the frequency domain, a straight correlation (lag=0) would be performed.

vi. Response Consistency

Another aspect of a brain response to a complex sound is the extent to which every presentation of the same acoustic stimulus (each a "trial") results in the same brain response. This may also be referred to as the stability of response. Response-consistency calculations may be performed in the time domain or the frequency domain. In addition, response-consistency calculations may be performed on an added waveform (e.g., opposing-polarity stimulus presentations are added) or a subtracted waveform (e.g., opposing-polarity stimulus presentations results subtracted/the responses to one of the polarities can be inverted).

In one approach, approximately half of the trials are randomly selected and averaged, and the remaining trials are averaged. The two sub-averaged waveforms are then correlated over a time window to determine their similarity. The time window can vary, as described above for stimulus-response correlation. Suitable methods for calculating a correlation score are known in the art and include, but are not limited to Pearson product-moment correlation, point-biserial, or Spearman techniques; correlation data may be Fisher-transformed to a z score before averaging. These steps are then repeated a number of different times, each repetition with a different random samplings of trials, and the correlation values from each repetition are averaged (arithmetic mean) to generate a final measure of inter-trial response consistency. The number of repetitions can vary, but should be selected to provide confidence that the final mean correlation value is a good representation of the underlying data. Another approach is not to maintain individual trials, but rather collect two discrete subaverages.

In certain embodiments, the amplitude of a response peak may be referenced to the amplitude of a non-stimulus-evoked portion of the response. An example of a non-stimulus-evoked portion of the response would be the interstimulus period, in other words the response to the silence between successive stimulus presentations. This interstimulus-period response would be considered background activity of the brain, and so computing the ratio response/interstimulus would be considered a signal to noise ratio (SNR).

vii. Difference Measures

A difference measure is a means of quantifying a change in a measure. For example, a difference measure may provide a means of quantifying a change in a response component in the same subject after time has passed, or after injury or intervention has taken place. A difference measure is also a means to quantify a difference in the same response component(s) to two (or more) different stimuli in the same subject. Additionally or alternatively, a difference measure may be applied to two measures within a single response. For example, the timing difference between peaks V and A, the phase-locking ratio between the $F_0$ and one or more harmonics, the amplitude ratio between multiple harmonics, the RMS amplitude difference between added- and subtracted-polarity responses, etc.

Difference measures may be expressed as a percent change (e.g., increase or decrease), as absolute terms (e.g., delay in msec; decrease in magnitude in μV, increase in frequency error in Hz, decrease in response consistency in r, etc.), or as a dB difference.

In embodiments where an acoustic stimulus comprises background noise, a difference measure may be a change in a response component in the presence of background noise as compared to the absence of background noise. For example, background noise is known to diminish response amplitudes, so one may wish to determine the percent reduction of $F_0$ amplitude when background noise is added to the acoustic stimulus. Any of the above listed measurements can be evaluated.

Examples of other contexts in which two or more responses could be compared include: changes in one or more frequencies in the sound (a /d/ with a high pitch vs a /d/ with a low pitch); different speech sounds (a /d/ compared to a /b/); sounds of varying amplitude modulation index, also known as modulation depth (the extent to which, in a complex signal, the ratio of the excursions of the modulated signal to the unmodulated signal, resulting in the degree of local amplitude envelope variation between two consecutive peaks in the signal); musical sounds of different pitch or timbre; etc.

II. Methods (a) Identifying Non-Penetrating Brain Injury and/or Classifying a Subject The present disclosure provides methods for identifying non-penetrating brain injury in a subject, as well as methods for classifying a subject that received a hit to the body that transmitted an impulsive force to the brain as either having a non-penetrating brain injury or not.

In one aspect, the method comprises analyzing one or more components of the subject's brain response to an acoustic stimulus comprising a complex sound; and identifying the subject as having a non-penetrating brain injury when a value for at least one component of the brain response is anomalous, wherein the component(s) is selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound is selected from those described in Section I(a). In some embodiments, a complex sound comprises a musical sound. In other embodiments, a complex sound comprises an environmental sound. In some embodiments, a complex sound comprises a speech sound or a non-speech vocal sound. In some embodiments, a complex sound comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are known in the art, and further detailed in Section I(a)(iii).

In another aspect, the method comprises analyzing one or more components of the subject's brain response to an acoustic stimulus comprising a complex sound; and identifying the subject as having a non-penetrating brain injury when a value for at least one component of the brain response is anomalous, wherein the component(s) is selected from the group consisting of fundamental frequency ($F_0$) and/or harmonics, neural timing of a sustained response peak, response amplitude over some or all of a consonant-vowel transition, and stimulus-response correlation over a time window that encompasses some or all of a sustained response. In some embodiments, the method further comprises analyzing one or more transient responses to an acoustic stimulus. The complex sound is selected from those described in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from the group consisting of /da/, /pa/, /ka/, /ta/, /ba/, and /ga/. Methods for recording a brain response to an acoustic stimulus are known in the art, and further detailed in Section I(a)(iii).

In another aspect, the method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) identifying the subject as having a non-penetrating brain injury when a value for at least one component of the brain response is anomalous, wherein the component(s) is selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound is selected from those described in Section I(a). In some embodiments, a complex sound comprises a musical sound. In other embodiments, a complex sound comprises an environmental sound. In some embodiments, a complex sound comprises a speech sound or a non-speech vocal sound. In some embodiments, comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are known in the art, and further detailed in Section I(a)(iii). [

In another aspect, the method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) identifying the subject as having a non-penetrating brain injury when a value for at least one component of the brain response is anomalous, wherein the component(s) is selected from the group consisting of fundamental frequency ($F_0$) and/or harmonics, neural timing of a sustained response peak, response amplitude over some or all of a consonant-vowel transition, and stimulus-response correlation over a time window that encompasses a sustained response. In some embodiments, the method further comprises analyzing one or more transient responses to an acoustic stimulus. The complex sound is selected from those described in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from the group consisting of /da/, /pa/, /ka/, /ta/, /ba/, and /ga/. Methods for recording a brain response to an acoustic stimulus are known in the art, and further detailed in Section I(a)(iii).

In another aspect, the method comprises analyzing one or more components of the subject's brain response to an acoustic stimulus comprising a complex sound; and classifying the subject as having a non-penetrating brain injury when a value for at least one component of the brain response is anomalous, wherein the component(s) is selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound is selected from those described in Section I(a). In some embodiments, a complex sound comprises a musical sound. In other embodiments, a complex sound comprises an environmental sound. In some embodiments, a complex sound comprises a speech sound or a non-speech vocal sound. In some embodiments, a complex sound comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are known in the art, and further detailed in Section I(a)(iii).

In another aspect, the method comprises analyzing one or more components of the subject's brain response to an acoustic stimulus comprising a complex sound; and classifying the subject as having a non-penetrating brain injury when a value for at least one component of the brain response is anomalous, wherein the component(s) is selected from the group consisting of fundamental frequency ($F_0$) and/or harmonics, neural timing of a sustained response peak, response amplitude over some or all of a consonant-vowel transition, and stimulus-response correlation over a time window that encompasses some or all of a sustained response. In some embodiments, the method further comprises analyzing one or more transient responses to an acoustic stimulus. The complex sound is selected from those described in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from the group consisting of /da/, /pa/, /ka/, /ta/, /ba/, and /ga/. Methods for recording a brain response to an acoustic stimulus are known in the art, and further detailed in Section I(a)(iii).

In another aspect, the method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) classifying the subject as having a non-penetrating brain injury when a value for at least one component of the brain response is anomalous, wherein the component(s) is selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. In some embodiments, the method further comprises analyzing one or more transient responses to an acoustic stimulus. The complex sound is selected from those described in Section I(a). In some embodiments, a complex sound comprises a musical sound. In other embodiments, a complex sound comprises an environmental sound. In some embodiments, a complex sound comprises a speech sound or a non-speech vocal sound. In some embodiments, comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are known in the art, and further detailed in Section I(a)(iii).

In another aspect, the method comprises (a) fitting the subject with electrodes to measure voltage potentials generated from the subject's brain; (b) administering to the subject an acoustic stimulus, wherein the acoustic stimulus comprises a complex sound; (c) recording voltage potentials from the subject's brain for at least the duration of the acoustic stimulus; (d) analyzing the voltage potentials to determine one or more components of the brain response; and (e) classifying the subject as having a non-penetrating brain injury when a value for at least one component of the brain response is anomalous, wherein the component(s) is selected from the group consisting of fundamental frequency ($F_0$) and/or harmonics, neural timing of a sustained response peak, response amplitude over some or all of a consonant-vowel transition, and stimulus-response correlation over a time window that encompasses some or all of a sustained response. In some embodiments, the method further comprises analyzing one or more transient responses to an acoustic stimulus. The complex sound is selected from those described in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from the group consisting of /da/, /pa/, /ka/, /ta/, /ba/, and /ga/. Methods for recording a brain response to an acoustic stimulus are known in the art, and further detailed in Section I(a)(iii).

In each of the above aspects, the subject may be symptomatic or asymptomatic.

In each of the above aspects, the term "anomalous value" refers to a deviation from the value for a control group or a normative value or a deviation from a previously established value for the subject (i.e., a "baseline value"), wherein the deviation exceeds the difference expected by chance. When an anomalous value is deviation from a value for a control group, the members of the control group may have never been diagnosed with a non-penetrating brain injury. Alternatively, the members of the control group may be a group of subjects that have never been diagnosed with a concussion. In another example, the control group may be a demographic subsample based on relevant information about the subject including, but not limited to, the subjects age and/or life experiences (e.g., number of years playing a contact sport, number of years in the military, number of years in a combat/war zone, number of car accidents, number of concussions, etc.). When an anomalous value is a deviation from a previously established value for the subject (i.e., a "baseline value"), the value may have been established before a subject was diagnosed with a non-penetrating brain injury including, but not limited to, a concussion or traumatic brain injury (TBI). Alternatively, a baseline value may have been established at a significant point in time—e.g., the start of a sports season, the start of a game or a competition, enlistment into the military, deployment to a combat/war zone, the start of employment, etc. A baseline value may also be the first available measurement for a subject. When an anomalous value is deviation from a value a normative value, the normative value may be obtained from published sources.

Suitable methods for determining whether a deviation exceeds the difference expected by chance are well-known in the art. For example, an analysis of statistical deviation may be based on probability distributions based on raw values or normalized values (e.g., z-scores, etc.), wherein one-half standard deviation or more (e.g. 1, 2, 3, 4, 5, or more) indicates a deviation that exceeds the difference expected by chance. Alternatively, a score or value may be converted to percentiles based on established value (e.g., an entire population's performance or based on a demographic subsample), wherein performance at or below the $50^{th}$ percentile, the $45^{th}$ percentile, the $40^{th}$ percentile, the $35^{th}$ percentile, the $35^{th}$ percentile, the $30^{th}$ percentile, the $25^{th}$ percentile, the $20^{th}$ percentile, the $15^{th}$ percentile, the $10^{th}$ percentile, or the $5^{th}$ percentile indicates a deviation that exceeds the difference expected by chance. In another example, a deviation that exceeds the difference expected by chance may be a difference determined by the minimum detectable change (MDC). The MDC is a statistic reflecting the smallest amount of deviation in a patient's score that ensures the change is not the result of measurement error, defined as 1.96 x the standard error of the mean on the test×√2. In another example, a deviation that exceeds the difference expected by chance may be determined by confidence intervals—a range of values in which there is a specified probability that the value of a measure lies within said range in a healthy population. For example, if a healthy population has a 90% confidence interval of 100-120, then in 90% of hypothetical cases we would predict performance in the population to fall within 100-120, so a score outside the confidence interval would be unlikely and anomalous. Common confidence interval ranges include 90%, 95%, and 99%. In another example, a deviation that exceeds the difference expected by chance may be determined by a statistical test to determine if a score falls outside of the range of expected based on frequentist probability theory, such as a student's t-test, an analysis of variance, a regression, a Mann-Whitney U test, a chi-square test, etc. In another example, a deviation that exceeds the difference expected by chance may be determined by a statistical test to determine if a score falls outside of the range of expected values based on Bayesian statistical theory. In another example, a deviation that exceeds the difference expected by chance may be a score that exceeds a threshold determined by research. This may be a categorical threshold (such as a body temperature over 100° qualifies as a fever) or it may be a threshold from a statistical algorithm that balances the probability of receiving true positive and true negative results. In embodiments where the deviation is value that exceeds a threshold from a statistical algorithm, the threshold typically produces at least an 80% sensitivity (true positive rate) and an 80% specificity (true negative rate), and has a strong predictive utility (e.g. as indicated by a Receiver Operating Characteristic (ROC)≥0.80, preferably, ≥0.85, more preferably ≥0.90; other types of predictive values include PPV, NPV, etc.). In another example, when the anomalous value refers to a deviation from a previously established value for the subject, a deviation that exceeds the difference expected by chance may be a difference in score that exceeds the threshold expected based on the test-retest performance in a healthy population. For example, if tests in a healthy population showed that an $F_0$ amplitude is expected to vary by 3 µV between tests, then a difference of about 4 µV between tests in a patient would be considered anomalous.

In each of the above aspects, "a value for at least one component of the brain response" includes one, two, three, four, five or more values for one or more components independently selected from the recited groups, wherein at least one component is an aspect of the frequency following response. Components that are an aspect of the frequency following response include fundamental frequency ($F_0$), harmonics, neural timing of a sustained response peak, response amplitude over a time window that encompasses some or all of a sustained response, and stimulus-response correlation a time window that encompasses some or all of a sustained response. As stated above, the method may further comprise analyzing one or more transient responses. In some embodiments, a transient response may be the timing or amplitude of an onset peak or onset response. In embodiments where the complex sound comprises one or more amplitude bursts, a suitable transient response may be the timing or amplitude of a transient response to the onset of one or more of the amplitude bursts.

In each of the above aspects, "a value for at least one component of the brain response" also includes embodiments where brain response values are combined together using a statistical model to produce a new measurement and the new measurement is anomalous, as defined above. A statistical model may have one or multiple steps. In embodiments where a statistical model has one step, two or more values are used in the single step. In embodiments where a statistical model has two or more steps, each step may consist of a single value or combine one or more values. For example, a first step may control for demographic factors that could have an effect on the FFR independent of brain injury. Non-limiting examples of values that may be included in the first step include age, gender, pre-existing medical conditions, background noise in the FFR (e.g., amplitude of non-stimulus related neural activity, such as in the interstimulus region, etc.), timing of the onset peak (e.g. wave V in response to a click), etc. One or more additional steps may then incorporate one or more values for a component that is an aspect of the frequency following response (e.g., two, three, four, five or more values for one or more components independently selected from the recited groups). Again, value(s) for one or more transient responses may be included with the FFR values. Suitable models should have a NPV and a PPV greater than about 80%, preferably greater than about 85%, more preferably greater than about 90%; and/or an ROC curve with an AUC value greater than about 0.80, preferably greater than about 0.85, more preferably greater than about 0.90.

In an exemplary embodiment, at least one anomalous value comprises $F_0$ and stimulus-response correlation over a time window that encompasses some or all of a sustained response. In another exemplary embodiment, at least one anomalous value comprises $F_0$ and amplitude of the onset response. In another exemplary embodiment, at least one anomalous value comprises stimulus-response correlation over a time window that encompasses some or all of a sustained response and amplitude of the onset response.

In embodiments where a value of fundamental frequency ($F_0$) is anomalous, the anomalous value may be $F_0$ amplitude, $F_0$ phase consistency, $F_0$ sharpness, $F_0$ frequency error, pitch tracking, or any combination thereof. Methods for determining these values are described in Section I(b)(i).

In embodiments where a value for neural timing of a response peak is anomalous, one, two, three, or more response peaks may have anomalous values. In certain embodiments, a value for neural timing of at least one sustained response peak is anomalous. As a non-limiting example, if the complex sound comprises /da/, the timing of peak A, peak D, or peak E may be anomalous, as well as any combination thereof. Methods for determining neural timing of a sustained response peak(s) are described in Section I(b)(iii).

In embodiments where response amplitude over some or all of the FFR is anomalous, the time window over which the response amplitude is calculated may be a portion of the FFR or the entire FFR. In preferred embodiments, the time window over which response amplitude is calculated includes at least one formant, preferably at least two formants (or equivalent of a formant for non-speech sounds). As a non-limiting example, when a complex sound comprises a consonant-to-vowel transition and response amplitude over the consonant-to-vowel transition is anomalous, the time range over which the response amplitude is calculated may optionally include unvoiced consonant release and/or the transient FFR component corresponding to the onset of voicing. When a complex sounds comprises more than one consonant-to-vowel transition, the response amplitude over the consonant-to-vowel transition may or may not be anomalous at each transition. Methods for determining the response amplitude over a FFR region are described in Section I(b)(iv).

In embodiments where a stimulus-response correlation value over a time window that encompasses some or all of a sustained response is anomalous, the anomalous value may be a time-domain measurement, a frequency-domain measurement, or both. In preferred embodiments, the time window includes at least one formant, preferably at least two formants (or equivalent of a formant for non-speech sounds). As a non-limiting example, when the complex sound is a speech sound, the time window may comprise a portion, or all, of a voiced response, including but not limited to a consonant-to-vowel transition, a voiced portion of a consonant transition, or a steady-state vowel portion. Methods for determining stimulus-response correlation values are described in Section I(b)(v).

(b) Determining a Change in a Non-Penetrating Brain Injury

The present disclosure also provides methods for determining a change in non-penetrating brain injury. These methods may be used to assess a subject's recovery from a non-penetrating brain injury to determine if the brain injury is worsening, improving, or has stayed the same. Subjects recovering from non-penetrating brain injury may or may not receive a therapeutic intervention. Non-limiting examples of types of therapeutic interventions include pharmaceutical, psychological (e.g. memory tests or brain "exercises"), auditory, and behavioral. For example, a subject recovering from non-penetrating brain injury may simply have been advised to rest and/or refrain from activities that may further worsen the non-penetrating brain injury. Alternatively, a subject recovering from non-penetrating brain injury may be involvement in a treatment program with the goal of speeding recovery or recovering aspects of brain function that would not have returned but for the treatment. A determination that the non-penetrating brain injury is worsening or has stayed the same may result in the start of a therapeutic intervention, a change in the type of therapeutic intervention, and/or or a modification of an existing therapeutic intervention; and/or advisement that the subject should refrain from activities that may further worsen the non-penetrating brain injury. A determination that the non-penetrating brain injury has improved or has stayed the same may result in the maintenance, change and/or discontinuation a therapeutic intervention, and/or may result in the subject being cleared to resume all activities.

In one aspect, the method comprises (a) analyzing one or more components of a subject's brain response to an acoustic stimulus comprising a complex sound; (b) re-testing the subject's brain response to the acoustic stimulus at a later time; and determining any differences in the one or more components from step (a); wherein the component(s) is selected from the group consisting of fundamental frequency ($F_0$) and/or harmonics, neural timing of a response peak, response amplitude over a time window that encompasses some or all of a sustained response, and stimulus-response correlation over a time window that encompasses some or all of a sustained response. If the absolute value of the difference is greater than would be expected by chance, there is a change in the non-penetrating brain injury. In some embodiments, a complex sound comprises a speech sound or a non-speech vocal sound. In some embodiments, comprises a first sound that transitions directly to a second sound, wherein the first sound has an attack substantially similar to an obstruent consonant and the second sound has a minimum of two formants held steady for one period of $F_0$.

Methods for recording a brain response to an acoustic stimulus are known in the art, and further detailed in Section I(a)(iii).

In another aspect, the method comprises (a) analyzing one or more components of a subject's brain response to an acoustic stimulus comprising a complex sound; (b) re-testing the subject's brain response to the acoustic stimulus at a later time; and determining any differences in the one or more components from step (a); wherein the component(s) is selected from the group consisting of fundamental frequency ($F_0$), neural timing of a sustained response peak, response amplitude over a time window that encompasses some or all of a consonant-to-vowel transition, and stimulus-response correlation over a time window that encompasses some or all of a sustained response. If the absolute value of the difference is greater than would be expected by chance, there is a change in the non-penetrating brain injury. In some embodiments, a component is an aspect of the frequency following response. The complex sound is selected from those described in Section I(a). In some embodiments, a complex sound comprises a musical sound. In other embodiments, a complex sound comprises an environmental sound. In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from the group consisting of /da/, /pa/, /ka/, /ta/, /ba/, and /ga/. Methods for recording a brain response to an acoustic stimulus are known in the art, and further detailed in Section I(a)(iii).

In another aspect, the method comprises two steps. The first step, i.e., step (a), tests a subject's brain response to an acoustic stimulus by: (1) fitting the subject with electrodes to measure voltage potentials generated from the subject's brain; (2) administering to the subject an acoustic stimulus, wherein the acoustic stimulus comprises a complex sound; (3) recording voltage potentials from the subject's brain for at least the duration of the acoustic stimulus; and (4) analyzing the voltage potentials to determine one or more components of the brain response; wherein the component(s) is selected from the group consisting of fundamental frequency ($F_0$), neural timing of a response peak, response amplitude over a time window that encompasses some or all of a sustained response, and stimulus-response correlation over a time window that encompasses some or all of a sustained response. The second step, i.e., step (b), re-tests a subject's brain response to the same acoustic stimulus by repeating steps (a)(1)-(4) and determining any differences in the one or more components from step (a). If the absolute value of the difference is greater than would be expected by chance, there is a change in the non-penetrating brain injury. The complex sound is selected from those described in Section I(a). In some embodiments, a complex sound comprises a musical sound. In other embodiments, a complex sound comprises an environmental sound. In some embodiments, a complex sound comprises a speech sound or a non-speech vocal sound. In some embodiments, comprises a first sound that transitions directly to a second sound, wherein the first sound has an attack substantially similar to an obstruent consonant and the second sound has a minimum of two formants held steady for one period of $F_0$. Methods for recording a brain response to an acoustic stimulus are known in the art, and further detailed in Section I(a)(iii).

In another aspect, the method comprises two steps. The first step, i.e., step (a), tests a subject's brain response to an acoustic stimulus by: (1) fitting the subject with electrodes to measure voltage potentials generated from the subject's brain; (2) administering to the subject an acoustic stimulus, wherein the acoustic stimulus comprises a complex sound; (3) recording voltage potentials from the subject's brain for at least the duration of the acoustic stimulus; and (4) analyzing the voltage potentials to determine one or more components of the brain response; wherein the component(s) is selected from the group consisting of fundamental frequency ($F_0$) and/or harmonics, neural timing of a sustained response peak, response amplitude over a time window that encompasses some or all of a consonant-to-vowel transition, and stimulus-response correlation over a time window that encompasses some or all of a sustained response. The second step, i.e., step (b), re-tests a subject's brain response to the same acoustic stimulus by repeating steps (a)(1)-(4) and determining any differences in the one or more components from step (a). If the absolute value of the difference is greater than would be expected by chance, there is a change in the non-penetrating brain injury. The complex sound is selected from those described in Section I(a). In some embodiments, a complex sound comprises a speech sound or a non-speech vocal sound. In other embodiments, a complex sound comprises a first sound that transitions directly to a second sound, wherein the first sound is an obstruent consonant and the second sound has a minimum of two formants held steady for one period of $F_0$. In other embodiments, a complex sound comprises a consonant, a consonant-to-vowel transition, and optionally a vowel. In other embodiments, a complex sound comprises a consonant, a consonant-to-vowel transition, and optionally a vowel, wherein the consonant is an obstruent stop consonant. In other embodiments, a complex sound comprises a consonant, a consonant-to-vowel transition, and optionally a vowel, wherein the consonant is an obstruent stop consonant and the vowel is a low, back vowel. In other embodiments, a complex sound comprises a speech syllable selected from the group consisting of /da/, /pa/, /ka/, /ta/, /ba/, and /ga/. Methods for recording a brain response to an acoustic stimulus are known in the art, and further detailed in Section I(a)(iii).

In each of the above aspects, the subject may be symptomatic or asymptomatic. For example, a subject may be asymptomatic at testing and re-testing. Alternatively, a subject may be symptomatic at testing and asymptomatic at re-testing. In another example, a subject may be symptomatic at testing and at re-testing, but one or more symptom may have improved when re-testing occurs. In another example, a subject may be asymptomatic at testing and symptomatic re-testing.

In each of the above aspects, the subject may be identified as having a non-penetrating brain injury in step (a) when a value for at least one component of the brain response is anomalous. In step (b), differences may only be calculate for those anomalous values, or may be calculated for all previously evaluated components. In the latter, components that did not change may be used as a control. Anomalous values and response components are described above in Section II(a), the disclosures of which are hereby incorporated into this section by reference.

In each of the above aspects "determining any differences in the one or more components" refers to calculating a difference measure. The direction of the change in the difference measure, i.e., positive or negative, indicates whether the change is an indication of improvement or deterioration in the non-penetrating brain injury. For example, an increase greater than would be expected by chance in response $F_0$ amplitude, $F_0$ phase consistency, $F_0$ sharpness, pitch tracking, response amplitude over the consonant-to-vowel transition, or stimulus-response correlation value indicates improvement, whereas a decrease greater than would be expected by chance in response $F_0$ frequency error or neural timing indicates improvement.

In each of the above aspects, "a value for at least one component of the brain response" includes one, two, three, four, five or more values for one or more components independently selected from the recited groups, wherein at least one component is an aspect of the frequency following response. "A value for at least one component of the brain response" also includes embodiments where brain response values are combined together using a statistical model to produce a new measurement. The related disclosures of Section (II)(a) are hereby incorporated into this section by reference, as are the disclosures related to the various aspects of the frequency following response.

III. Systems

Figure 6:
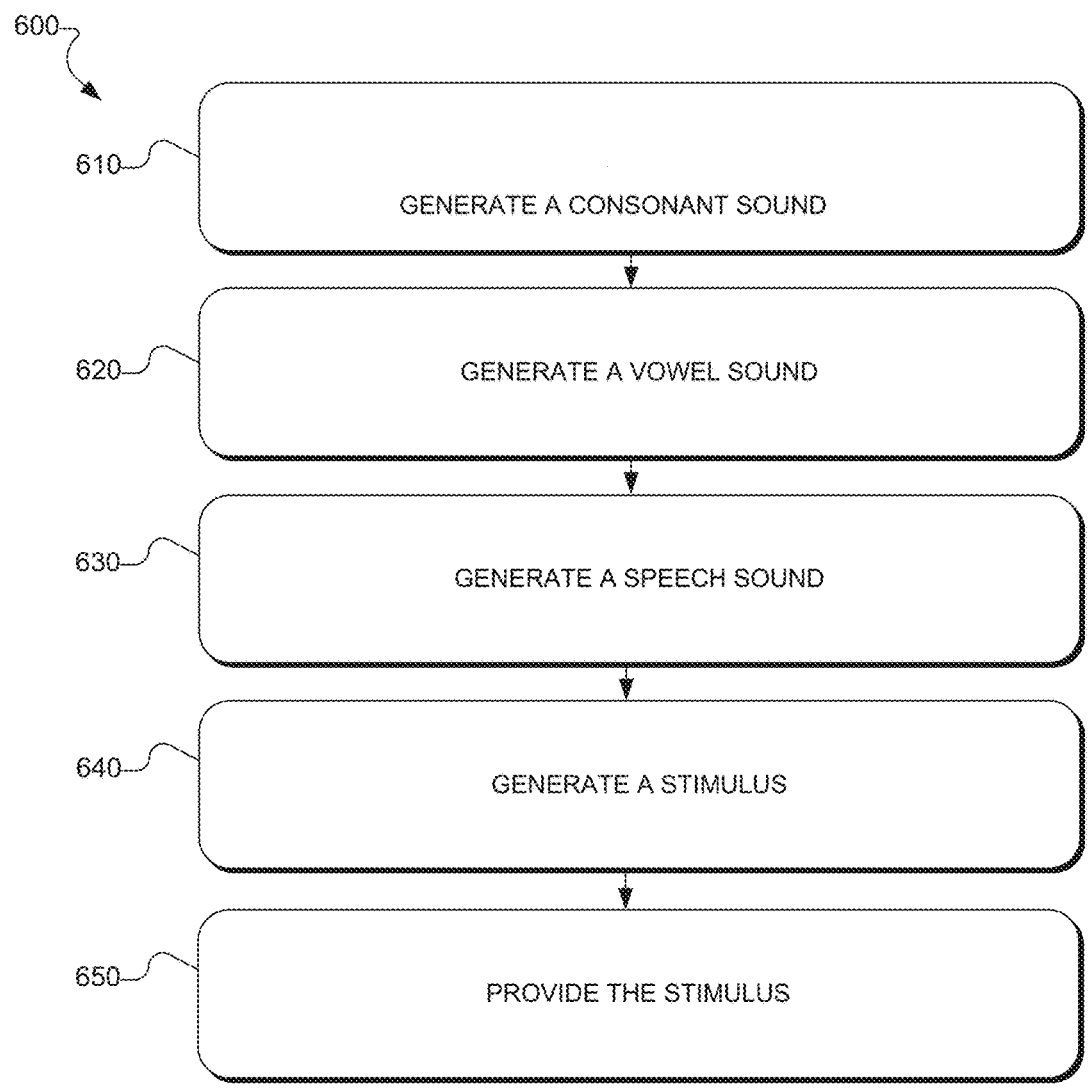
FIG. 6 illustrates an example process 600 for generating stimuli and processing brain response data to identify or otherwise determine non-penetrating brain injuries.
Figure 7:
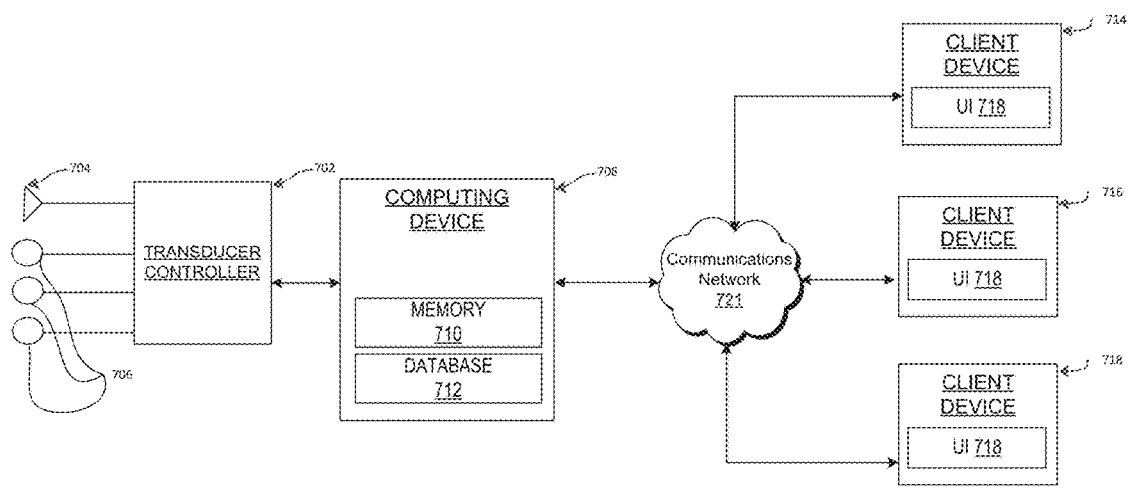
FIG. 7 illustrates an example of a computing environment and/or computing system 700 that automatically transmits acoustic stimuli, receives and processes brain response data, and automatically generates indications of non-penetrating brain injuries based on the brain response data.
Figure 8:
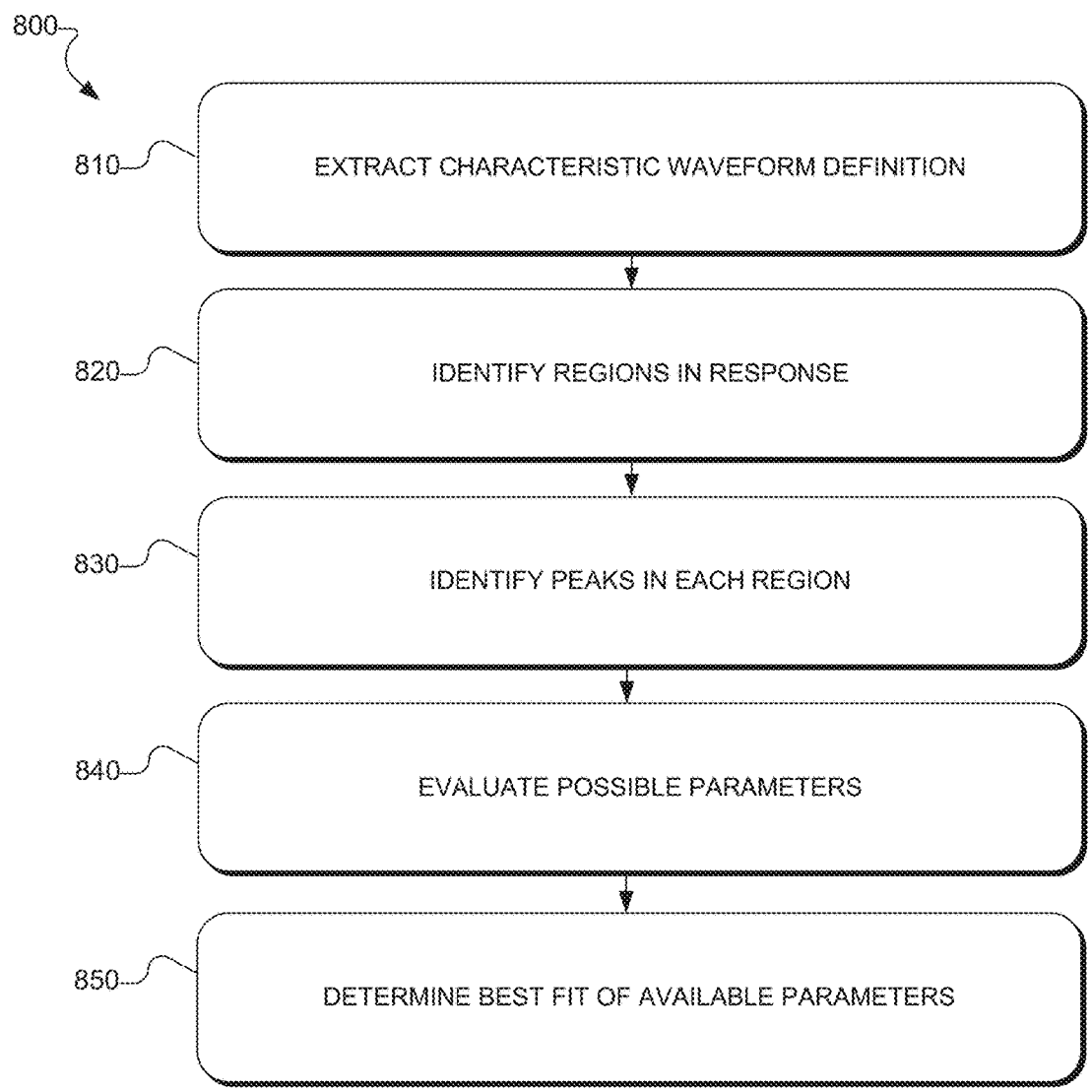
FIG. 8 illustrates an example process 800 for generating stimuli and processing brain stem response data to identify or otherwise determine non-penetrating brain injuries.

An illustrative process and system for automatically generating acoustic stimuli and processing brain response data to identify non-penetrating brain injuries in subjects is depicted in FIG. 6-8. In particular, FIGS. 6 and 8 illustrate example processes 600 and 800 for generating stimuli and processing brain stem response data to identify or otherwise determine non-penetrating brain injuries. FIG. 7 illustrates a computing environment and/or computing system 700 that automatically transmits acoustic stimuli, receives and processes brain response data, and automatically generates indications of non-penetrating brain injuries based on the brain response data. More specifically, FIG. 7 illustrates a computing environment and/or computing system 700 including a server computing device 708 operating in conjunction with various other hardware and/or software components that may be used to perform or otherwise execute the process 600 and process 800.

Referring initially to FIG. 7, the computing environment 700 includes a transducer controller 702 functionally coupled to an acoustic transducer 704 and one or more electrodes 706. More specifically, the transducer controller 702 represents a computing and/or processing device that delivers a stimulus to the acoustic transducer 704. Additionally, the transducer controller 702 may receive and process brainwave signal information from the one or more electrodes 706. The transducer controller 702 may be any suitable stimulus delivery and data acquisition system, including PC-based stimulus delivery and data acquisition systems such as those available from Bio-logic Systems Corporation or Compumedics. The acoustic transducer 704 may be an insert earphone such as the ER-3 insert earphone available from Etymotic Research, Elk Grove, Ill. The one or more electrodes 706 may be Ag—AgCl scalp electrodes, which may be positioned on the test subject from Cz (active) to ipsilateral earlobe (reference) with forehead ground.

The transducer controller 702 may be functionally connected to a computing device 708 including a memory 710 within which instructions are retained directing the operation of the computing device 708 for carrying out the herein described methods and processes (e.g., process 600 of FIG. 6 and process 800 of FIG. 8). More specifically, the computing device 708 automatically generates a test stimulus signal, communicates the test stimulus signal to the transducer controller 702 for generation of an acoustic stimulus that is presented or otherwise provided to the test subject via the acoustic transducer 704. The computing device 708 may obtain brain response data via the electrodes 706 and the transducer controller 702. The brain response data may be stored within the memory 710 and/or stored or otherwise maintained in a database 712.

The computing device 708 may transmit the brain response data to one or more client devices 714-720. The or more client devices 714-720 functionally communicate with the computing device 708 through a communications network 721, which may be the Internet, an intranet, and Ethernet network, a wireline network, a wireless network, and/or another communication network. The one or more client devices 714-720 may be a personal computer, work station, mobile device, mobile phone, tablet device, processor, and/or other processing device capable of implementing and/or executing processes, software, applications, etc., that includes network-enabled devices and/or software, such as user-interface 718 for communication over the communications network 112 (e.g., browsing the internet). Additionally, the one or more client device(s) 714-720 may include one or more processors that process software or other machine-readable instructions and may include a memory to store the software or other machine-readable instructions and data.

The database 712 may include one or more data structures used to stored data for analysis of the acquired brain response data. For example, the database 712 may contain one or more data structures containing normative response data to which the acquired brain response data may be compared to provide comparison data. The database 712 may further contain criteria data for evaluating the comparison data for determining the existence of a non-penetrating brain injury.

Referring now to FIG. 6, as stated above, FIG. 6 illustrates a process 600 for generating and applying a stimulus to a subject. The stimulus sound can include any of a variety of real and/or synthetic sounds including a frequency sweep over time against a background (e.g., a sound including one or more transitions based on rapid changes in frequency over a period of time, a sound including a formant transition built with complementary background noise, etc.). One example of a stimulus, illustrated in the example method of FIG. 2, is a consonant-vowel combination against background noise.

At block 610, a consonant sound of a first duration is generated. For example, a /d/, /g/, /c/, etc., is selected as the consonant sound to form part of the audio stimulus to elicit a response from the subject.

At block 620, a vowel sound of a second duration is generated. In certain examples, the second duration is longer than the first duration. That is, the vowel sound is played longer in the stimulus than the consonant sound. For example, an /a/, /i/, /o/, /u/, etc., is selected as the vowel sound to accompany the /d/, /g/, /c/, etc., selected as the consonant sound to form part of the audio stimulus to elicit a response from the subject.

At block 630, a speech sound is generated by combining the consonant sound followed by the vowel sound. For example, the consonant sound and vowel sound are combined by placing the vowel sound after the consonant sound to form the speech sound to be provided in the stimulus. In other examples, the consonant sound follows the vowel sound to form the speech sound.

At block 640, the stimulus is generated by mixing a background noise with the speech sound to generate the stimulus. For example, the background noise includes a plurality of voices talking at the same time and/or approximately the same time to create a human background noise over which the stimulus can be played. In certain examples, the background noise is of a third duration which is longer than the second duration (and, therefore, also longer than the first duration).

At block 650, the stimulus is provided for output with respect to the subject. For example, the stimulus can be output as a six-formant stop consonant constructed in a synthesizer, such as a Klatt-based synthesizer at 20 kHz, etc. In certain examples, following an initial stop burst, a consonant transition (e.g., 50 ms from /d/ to /a/, etc.) during which lower formants (e.g., the lower three formants) shift in frequency (e.g., F1 400-720 Hz, F2 1700-1240 Hz, F3 2580-2500 Hz, etc.). In these examples, the lower three formants are steady for the subsequent vowel (e.g., 120 ms at /a/), and the fundamental frequency and upper three formants are steady through the stimulus (e.g., F0 100 Hz, F4 3300 Hz, F5 3750 Hz, F6 4900 Hz, etc.). The stimulus is presented against a noise or "babble" track (e.g., six voices speaking semantically anomalous English sentences at a +10 SNR, etc.). In certain examples, the babble track loops continuously since there is no phase synchrony between the onsets of the speech sound and the noise. In certain examples, the stimulus formed from the speech sound and noise is mixed into a single channel that is presented to a single ear of the subject (e.g., the right ear of the subject at 80 dB of sound pressure level (SPL) in alternating polarities through electromagnetically-shielded insert earphones, etc.). In certain examples, stimulus presentation can be controlled with a defined interstimulus interval (e.g., 61 ms, 81 ms, etc.) in a plurality of sweeps (e.g., 4200 sweeps, 6300 sweeps, etc.). While the process 600 described above describes a specific a complex sound that contains a consonant to vowel transition, it is contemplated that other complex sounds may be used, such as the complex sounds described above in Section I(a)(i) and Section (a)(iv) above.

Referring now to FIG. 8, a process 800 for analyzing a response to a stimulus from one or more subjects is provided. At block 810, a characteristic waveform definition is extracted from the received response. For example, a time-locked average of one or more subject responses (e.g., inter-response and intra-response averaging) is computed to amplify common features and reduce noise to increase signal-to-noise ratio (SNR) of the characteristic waveform.

At block 820, the characteristic waveform of the response is processed to identify distinct regions within the response. For example, a consonant-vowel complex sound includes three regions: a) a consonant sound region, b) a transition region between the consonant and the vowel, and c) a vowel sound region. These regions may be the same length and/or may be of varying lengths with respect to each other. For example, the vowel sound region may be of longer duration than the consonant sound region, and the transition region may be shorter than the consonant sound region.

The vowel region is readily identified by analyzing an end of the response to identify a series of evenly spaced peaks that are the brain's response to the fundamental frequency of the vowel sound. Using peak finding techniques such as a windowed, filtered, maxima and/or minima, etc., peaks can be identified and compared for consistency of temporal spacing. Additionally, this technique can be informed by a-priori knowledge about the fundamental frequency of a sound so that an expected spacing between the peaks is known. The vowel region is then defined as the temporal region between the first occurring peak in this train of peaks and the end of the response.

The consonant region (e.g., a region of the first onset peak for the stimulus) can be identified using similar peak finding techniques as those used to find the vowel region. The consonant region is defined as a region between the first large peak, known as the onset peak, in the characteristic waveform, and the next peak that exceeds the onset peak's amplitude. The location of both peaks can be further informed by the a-priori knowledge of the stimulus timing and experiential knowledge of a brain's latency in response to onset of sound stimuli.

Once the consonant and vowel regions have been defined, the transition region is defined as the response in temporal period between the end of the consonant region and the beginning of the vowel region. Peaks within this region can also be identified using the same windowed peak-picking algorithm used in identifying peaks in the other two regions.

At block 830, one or more peaks are identified within the determined regions of the response. For example, peaks can be identified within a vowel response region. Using information about the temporal location of peaks within the vowel region from the characteristic response as a template, peak searching can be seeded within the same region on individual responses to the same stimulus. By allowing the peak search to shift slightly within a range relative to the expected location, individual differences in temporal latency from the characteristic response can be captured and used for subsequent analysis. Similarly, individual differences in peak location with the transition region may be captured and used for subsequent analysis.

At block 840, parameters are evaluated based on the regions and determined peak information. For example, by analyzing the response to identify various aspects of the response (e.g., regions of the response, peaks within each region, etc.), parameters (e.g., cABR parameters) can be evaluated to build a model for determination of the behavioral outcome of interest. In certain examples, parameters can be added and/or removed and tested with respect to the developing model. If the parameter improves the model fit, the parameter can be associated with the model. If, however, the parameter worsens or otherwise fails to improve the model fit, the parameter is not associated with the model.

In certain examples, one or more databases and/or other data stores include data and results from testing of different cABR parameters on different demographics. Databases and/or data stores can also include industry-standard behavioral test results obtained from subjects of various ages for comparison in building and evaluating a model.

At block 850, a best fit of available parameters is determined for a desired behavioral outcome model. For example, in determining a best fit, there are many processes by which a combination of independent variables (or features) can be derived so that combination best predicts a set of dependent variables (outcome measures) across a population of individuals. One such method is regression ((e.g., general linear models such as hierarchical regression, logistic regression, ordinary least squares regression, etc.) but other methods include neural networks, latent variable modeling, support vector machines, genetic expression programming, etc. A combination of those independent variables that best predicts the values of the outcome measures can be considered a predictive model of those outcome measures (also referred to as behavioral outcomes) for a population (e.g., for individuals in that population), given a population that is appropriately-large for the chosen statistical approach. In certain examples, combinations of independent variables can be linear combinations and/or non-linear combinations. Additionally, as discussed above, some variables may provide no substantive contribution to the model and may be discarded to simplify the model's complexity. One process, known as LASSO (Least Absolute Shrinkage and Selection Operator) analysis, is a regression analysis method that performs variable selection and regularization to generate a desired model at varying degrees of complexity (e.g., with more/less independent variables contributing). Resulting selected parameters can be calculated and used to generate the desired behavioral outcome model, for example. While the process 800 described above describes a specific a complex sound that contains a consonant to vowel transition, it is contemplated that other complex sounds may be used, such as the complex sounds described above in Section I(a)(i) and Section (a)(iv) above.

Figure 9:
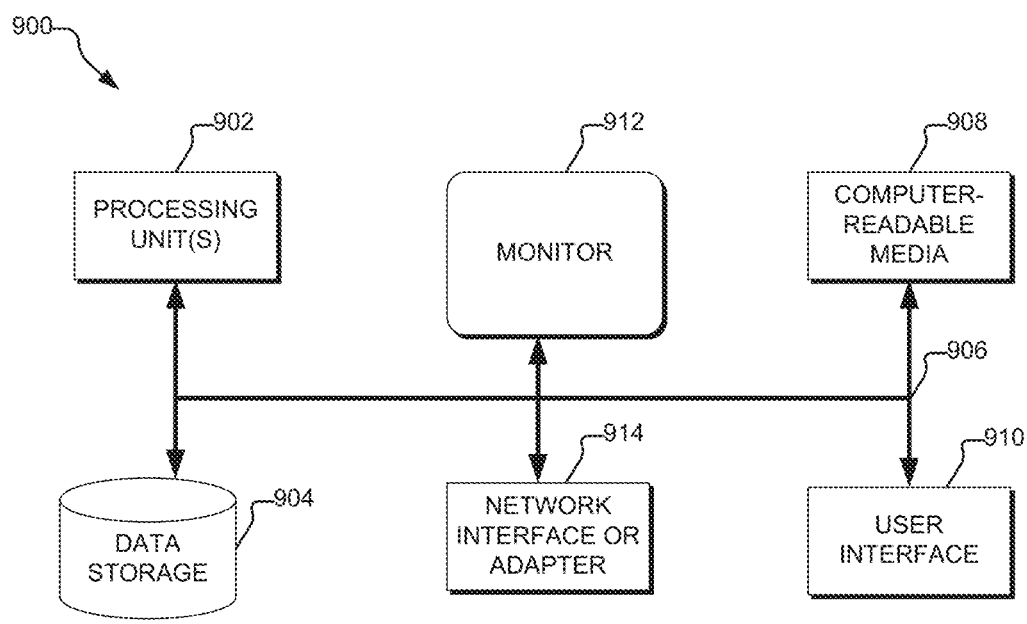
FIG. 9 illustrates an example of a suitable computing and networking environment 900 that may be used to implement various aspects of the present disclosure described in FIGS. 6 and 7 (e.g. the computing device 702 and corresponding components).

FIG. 9 illustrates an example of a suitable computing and networking environment 900 that may be used to implement various aspects of the present disclosure described in FIGS. 6 and 7 (e.g. the computing device 702 and corresponding components). As illustrated, the computing and networking environment 900 includes a general purpose computing device 900, although it is contemplated that the networking environment 900 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 900 may include various hardware components, such as a processing unit 902, a data storage 904 (e.g., a system memory), and a system bus 906 that couples various system components of the computer 900 to the processing unit 902. The system bus 906 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 900 may further include a variety of computer-readable media 908 that includes removable/non-removable media and volatile/nonvolatile media, but excludes transitory propagated signals. Computer-readable media 908 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/ data and which may be accessed by the computer 900. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 904 includes computer storage media in the form of volatile/nonvolatile memory such as read only memory (ROM) and random access memory (RAM). A basic input/output system (BIOS), containing the basic routines that help to transfer information between elements within the computer 900 (e.g., during start-up) is typically stored in ROM. RAM typically contains data and/or program modules that are immediately accessible to and/or presently being operated on by processing unit 902. For example, in one embodiment, data storage 904 holds an operating system, application programs, and other program modules and program data.

Data storage 904 may also include other removable/non-removable, volatile/nonvolatile computer storage media. For example, data storage 904 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 9, provide storage of computer-readable instructions, data structures, program modules and other data for the computer 900.

A user may enter commands and information through a user interface 910 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 902 through a user interface 910 that is coupled to the system bus 906, but may be connected by other interface and bus structures, such as a parallel port, game port or a universal serial bus (USB). A monitor 912 or other type of display device is also connected to the system bus 906 via an interface, such as a video interface. The monitor 912 may also be integrated with a touch-screen panel or the like.

The computer 900 may operate in a networked or cloud-computing environment using logical connections of a network interface or adapter 914 to one or more remote devices, such as a remote computer. The remote computer may be a personal computer, a server, a router, a network PC, a peer device or other common network node, and typically includes many or all of the elements described above relative to the computer 900. The logical connections depicted in FIG. 9 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 900 may be connected to a public and/or private network through the network interface or adapter 914. In such embodiments, a modem or other means for establishing communications over the network is connected to the system bus 906 via the network interface or adapter 914 or other appropriate mechanism. A wireless networking component including an interface and antenna may be coupled through a suitable device such as an access point or peer computer to a network. In a networked environment, program modules depicted relative to the computer 900, or portions thereof, may be stored in the remote memory storage device.

EXAMPLES

The following examples illustrate various iterations of the invention. However, those of skill in the art should, in light of the present disclosure, appreciate that many changes can be made in the specific embodiments which are disclosed and still obtain a like or similar result without departing from the spirit and scope of the invention.

Example 1. Methods for Examples 2 to 8

The following methods were used for examples 2 to 8.
Experimental Design & Subjects.

Two groups of children participated in this study. Inclusionary criteria included normal hearing, no neurologic disease, and no history of severe traumatic brain injury (TBI). Descriptive statistics for both groups are provided in Table 1.

The concussion group (N=20, 6 males, mean age=13.39 yr, SD=1.79 yr) was recruited from the Institute of Sports Medicine at Ann & Robert H. Lurie Children's Hospital of Chicago, a specialty clinic. Children in this group met clinical diagnostic criteria for a concussion[6] and participated in the experiment following their medical evaluation by a sports medicine physician (CRL) with expertise in concussion diagnosis and management. On average, they were evaluated 27 days after their injury (mean=26.7 days, SD, 15.3 days, range: 6-56 days). Injuries were attributed to basketball (N=1), cheerleading (N=2), football (N=3), hockey (N=2), soccer (N=1), softball (N=2), volleyball (N=1), and other recreational activities (N=8). Thirteen of the children reported a history of a previous concussion. Six of the children had a computerized tomography (CT) scan of the head and two had magnetic resonance imaging scans of the head; all were normal, except one had a preexisting cyst and one child had a slight odontoid asymmetry. Because the concussion group was recruited and tested at a specialty clinic the data collection could not be blinded to subject group.

A subset of the subjects from the concussion group returned to the clinic for follow-up and were retested (N=11, 3 males, mean age=13.25 yr, SD 1.93 yr; average test-retest interval: 34.9 days, SD 15.7 days, range 11-56 days). Although only one of the subjects was fully recovered at this visit, they were seen by the clinical team as a part of concussion monitoring. Two of them reported that their symptoms had abated since the first evaluation, and at the second evaluation one was cleared to resume normal activities.

The control group (N=20, 6 males, mean age=13.64 yr, SD 1.87 yr) was recruited from the community through in-school flyers and word of mouth; none reported a history of brain injury. The groups were matched with respect to age (t(38)=0.092, p=0.927, Cohen's d=0.029) and had the same distribution of males and females.

All the subjects passed a hearing screening involving distortion product otoacoustic emission screening, suggesting normal outer hair cell function in the cochlea (>6 dB signal-to-noise ratio from 0.4-5 kHz). All subjects had normal auditory brain responses (ABR) to a 100 μs click presented at 80.4 dB SPL to the right ear, and the two groups had similar ABR onset response timing (Wave V: t(38)=0.261, p=0.795, Cohen's d=0.083). The comparable click-evoked response timing suggests that concussions do not compromise signal transduction through the peripheral auditory pathway; this observation is consistent with previous research[1].

Neurophysiology.

Frequency-following responses (FFRs[2]) were elicited by a 40 msec sound /d/ synthesized in a Klatt-based synthesizer (SenSyn, Sensimetrics Corporation, Malden, Mass.). The stimulus begins with a plosive burst during the first 10 msec, with a 5 msec voice-onset time. During the voiced period of the stimulus, the fundamental frequency ($F_0$) rises linearly from 103→125 Hz while the formants shift linearly as follows: $F_1$ 220→720 Hz, $F_2$ 1700→1240 Hz, and $F_3$ 2580→2500 Hz. The last two formants are steady throughout the stimulus ($F_4$ 3600 Hz, $F_{5\ 4500}$ Hz). Although the stimulus is brief and there is no vowel, it is perceived as the consonant-vowel (CV) syllable /da/. Normative data are available for responses to this stimulus in normal-hearing individuals from birth to age 72 yr[3]. Stimuli were delivered and responses were collected through a Bio-logic Navigator Pro System (Natus Medical Inc., Mundelein, Ill.). FFRs were measured in a vertical montage with three Ag—AgCl electrodes (Cz active, Fpz ground, right earlobe reference). Stimuli were delivered to the right ear in alternating polarities at 80.4 dB sound pressure level at 10.9 Hz through an electromagnetically-shielded insert earphone (Etymotic Research, Elk Grove Village, Ill.). Responses were filtered online from 100-2000 Hz (second-order Butterworth) and sampled at 12 kHz. Online artifact rejection was employed at ±23 μV, and two blocks of 3000 artifact-free stimulus presentations were averaged with a 75 msec recording epoch (including a 15.8 msec non-stimulus period, which served as a control measure of background noise).

Concussion Symptom Severity.

Children in the concussed group completed the Postconcussion Symptom Scale (PCSS[7,8]) to report their symptom load. For each of the 19 symptoms, encompassing neurocognitive, emotional, and somatic aspects of concussion symptomology, subjects indicated on a Likert scale of 0-6 the intensity of each symptom. The PCSS total score is the sum of the scores for each symptom, and represents the subject's symptom load. Higher scores reflect greater symptom loads. Total PCSS scores at test one ranged from 0 to 71 (mean 31.5, SD 21.9) and, in the eleven children who returned for a follow-up test, from 0 to 52 at test two (mean 12.8, SD 15.2). Headache was the most frequently reported symptom (test one: 17/20 concussion patients; follow-up test: 7/11 patients). Also reported were difficulty concentrating (test one: 16/20 concussion patients; follow-up test: 7/11 patients), drowsiness (test one: 14/20 concussion patients), and photosensitivity (test one: 14/20). No patients reported nausea or vomiting.

Data Analyses.

Neurophysiological responses were analyzed with respect to amplitude, timing, accuracy, and $F_0$/pitch processing[2,3]. The fundamental frequency ($F_0$) amplitude was defined as the spectral amplitude between 75 to 175 Hz, which corresponds to the $F_0$ of the stimulus; this was compared to harmonic coding (175-750 Hz). To determine spectral amplitudes, the response was converted to the frequency domain (from 19.5 to 44.2 msec; fast Fourier transformation with a 2 msec Hanning window). As a complementary analysis to determine the strength of pitch coding, an autocorrelation was run from 19.5 to 44.5 msec (sliding window, 20 msec bins, 1 msec of overlap) and the mean correlation at a lag corresponding to the average period of the stimulus was determined[5]. To determine response amplitude over the consonant-vowel transition, the root-mean-squared amplitude of the response was computed from 19.5 to 44.2 msec (corresponding to the voiced period of the stimulus). To determine timing, the latencies of several stereotyped response peaks were identified. Peaks were identified on the final average in consultation with a normative template and two subaverages. To determine accuracy, the stimulus was filtered to match the response (100-2000 Hz, second-order Butterworth) and each child's response was cross-correlated to the filtered stimulus (from 19.5 to 44.2 msec; the maximum correlation at an appropriate lag was obtained and Fisher-transformed to z scores for statistical purposes). All statistics reported reflect two-tailed tests.

Figure 2A:
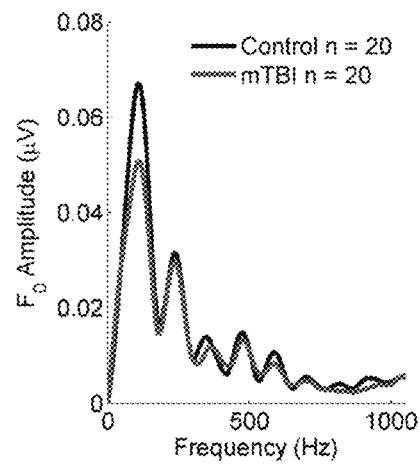
FIG. 2A-D depicts graphs showing that the neural coding of the fundamental frequency ($F_0$, peak at around 100 Hz), but not harmonic cues (peaks from 200 to 1000 Hz), is impaired in children with a concussion. (A,B) The concussed children (red) have smaller responses to the pitch of a talker's voice than their non-concussed peers (black). A regression predicting symptom load from neural processing of the $F_0$ (controlling for sex) illustrates a high degree of similarity between reported and predicted symptoms (C) and the majority of children in the concussion group are at or below the 50th percentile (D) relative to established norms. (B: Error bars represent±1 S.E.M.; D: Horizontal solid lines represent±1 SD of normative data, horizontal dashed lines represent±1.5 SDs of normative data, and horizontal dotted lines represent 2 SDs of normative data).
Figure 2B:
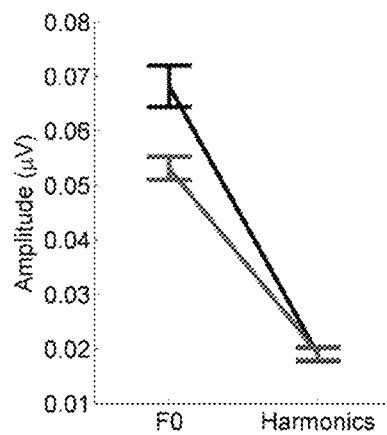
Figure 2C:
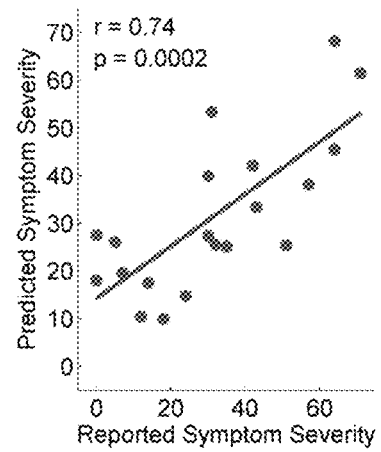
Figure 2D:
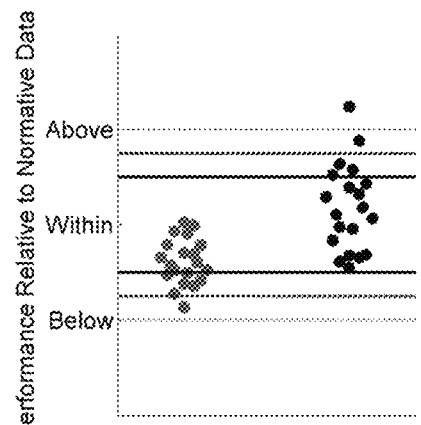

Example 2. Neural Coding of the Fundamental Frequency is Disrupted Following Concussion The children who sustained a concussion had smaller responses to the $F_0$ than their peers in the control group (by ≈35%), but the groups had similar harmonic processing (group×frequency interaction, F(1, 38)=16.554, p<0.001, $\eta^2$=0.303; post-hoc group differences for $F_0$, t(38)=3.607, p=0.001, Cohen's d=1.223; harmonics, t(38)=1.056, p=0.298, Cohen's d=0.329; FIG. 2A/B). To complement this analysis, the strength of pitch coding was determined by performing autocorrelations on the FFRs[5]. Children with a concussion had poorer pitch coding than their peers from the control group (t(38)=2.773, p=0.009, Cohen's d=1.14; see Table 1). Within the concussion group, children who reported the highest symptom load had the smallest responses to the $F_0$ (regression controlling for sex, $R^2$=0.548, F(2, 19)=10.287, p=0.001; $\beta_{F0}$=−0.712, p=0.001).

TABLE 1

Descriptive statistics for the concussion and control groups. Means are reported with standard deviations.

|  | Control (N = 20) | Concussion (N = 20) | Concussion-Retest (N = 11) |
|---|---|---|---|
| Age (yr) | 13.64 (1.87) | 13.69 (1.79) | 13.25 (1.29) |
| Male:Female | 6:14 | 6:14 | 3:8 |

TABLE 1-continued

Descriptive statistics for the concussion and control groups. Means are reported with standard deviations.

|  |  | Control (N = 20) | Concussion (N = 20) | Concussion-Retest (N = 11) |
|---|---|---|---|---|
| Click V Latency (msec) |  | 5.64 (0.22) | 5.66 (0.22) | 5.66 (0.30) |
| Amplitude over CV Transition (µV) |  | 0.09 (0.02) | 0.07 (0.03)* | 0.07 (0.04) |
| Timing (msec) | V | 6.52 (0.25) | 6.62 (0.24) | 6.82 (0.41) |
|  | A | 7.42 (0.27) | 7.65 (0.31)* | 7.82 (0.41) |
|  | D | 22.29 (0.30) | 22.63 (0.59)* | 22.80 (0.92) |
|  | E | 30.80 (0.40) | 31.23 (0.44)** | 31.09 (0.30) |
|  | F | 39.37 (0.35) | 39.52 (0.44) | 39.55 (0.52) |
|  | O | 48.24 (0.37) | 48.13 (0.38) | 48.18 (0.41) |
| Stimulus-response correlation (Pearson's r) |  | 0.15 (0.10) | 0.08 (0.04)* | 0.08 (0.05) |
| Spectral amplitude (µV) | $F_0$ | 0.068 (0.017) | 0.048 (0.019)*** | 0.062 (0.015)† |
|  | Harmonics | 0.019 (0.005) | 0.017 (0.007) | 0.018 (0.004) |
| Pitch coding(Pearson's r) |  | 0.30 (0.08) | 0.24 (0.07)** | 0.24 (0.09) |

Concussion vs. Control group:
*$p < 0.05$,
**$p < 0.01$,
***$p = 0.001$;
Concussion Subgroup Test 1 vs. Test 2
†$p < 0.05$.

Example 3. Diminished Neural Responses to Speech Following Concussion

Figure 3A:
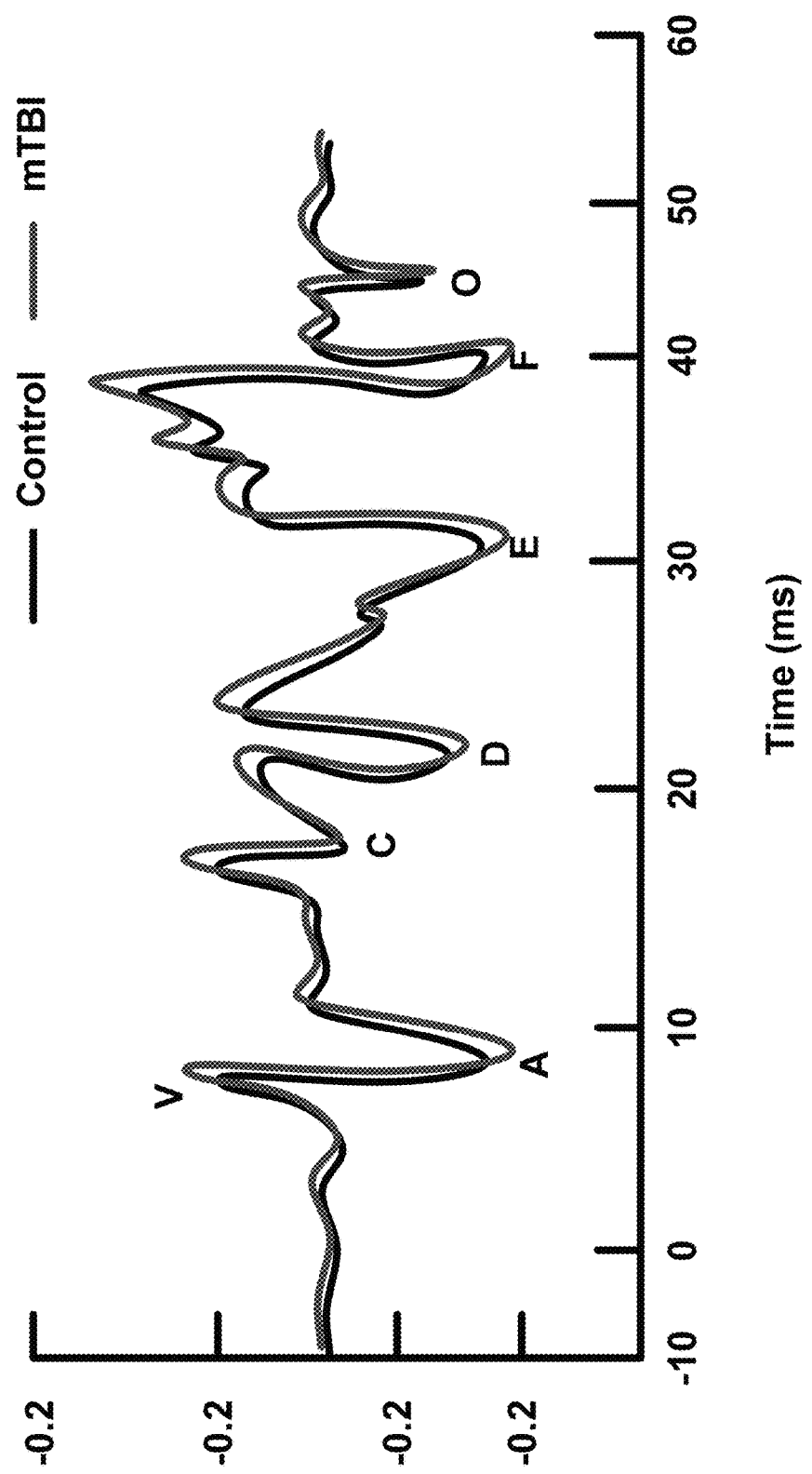
FIG. 3A-B depicts graphs showing children with a concussion have smaller and slower neural response to speech. Comparison of the grand average brain response (A) for the concussion (red) and control groups (black). Brain responses of concussed children are smaller over the consonant-vowel transition (A,B) and slower (A) than those of their non-concussed peers. Error bars represent ±1 S.E.M.
Figure 3B:
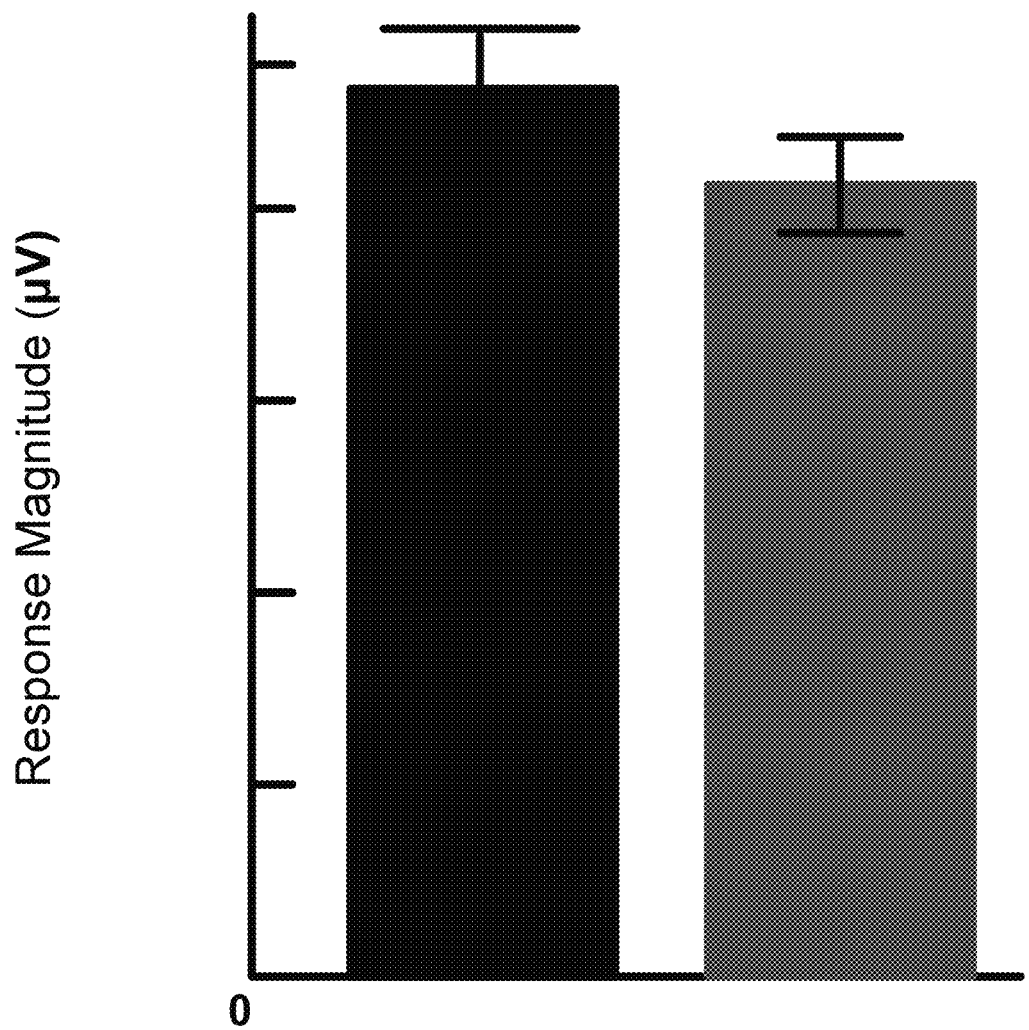

The next analysis considered the amplitude of the neural response over the CV transition. Children who sustained a concussion had smaller responses to speech than their uninjured peers (t(38)=2.382, p=0.022, Cohen's d=0.832; FIG. 3A/D). Because the response to the $F_0$ dominates the time-domain FFR, this may be a corollary of the diminished $F_0$.

Example 4. Slower Neural Responses to Speech Following Concussion

The next analysis considered the timing of neural processing by asking how quickly the auditory system responds to several cues in the speech sound, which are represented by characteristic peaks in the FFR. The children who sustained a concussion had slower responses to some, but not all, stimulus features (group×peak interaction, F(5, 30)=5.091, p=0.002, $\eta^2$=0.459; FIG. 3A). Post-hoc tests comparing individual peaks showed that children in the concussion group had responses nearly 0.4 msec slower than their uninjured peers for three of the six response peaks, reflecting the coding of the periodicity (note not all peaks were detectable in every child; Peak A, t(38)=2.542, p=0.015, Cohen's d=0.804; Peak D, t(36)=2.258, p=0.030, Cohen's d=746; Peak E, t(37)=3.301, p=0.002, Cohen's d=1.059; FIG. 3A). While a timing discrepancy of 0.4 msec is small, in the context of the subcortical auditory system it is clinically significant. These particular peaks reflect the coding of the $F_0^4$, suggesting that both the amplitude and the timing of $F_0$-coding is disrupted.

However, the two groups had similar timing to the onset of the sound (Peak V, t(32)=1.358, p=0.183, Cohen's d=0.429), for the last peak reflecting the transition into a steady state vowel (Peak F, t(38)=1.169, p=0.250, Cohen's d=0.370), and in response to the offset of the sound (Peak O, t(36)=0.876, p=0.387, Cohen's d=0.284; FIG. 3A). Thus, it appears concussions impart a selective timing delay that only affects the neural coding of certain speech features. Specifically, it appears concussions target the coding of periodicity ($F_0$) cues in speech while sparing transients (such as plosive onset bursts). Each individual's FFR was correlated to the stimulus to achieve a "global" measure of the integrity of neural processing. Children in the concussion group, on average, had less accurate neural coding of the speech sound than their uninjured peers (t(38)=2.660, p=0.011, Cohen's d=0.841).

Example 5. Less Accurate Neural Responses to Speech Following Concussion

Each individual's FFR was correlated to the stimulus to achieve a "global" measure of the integrity of neural processing. Children in the concussion group, on average, had less accurate neural coding of the speech sound than their uninjured peers (t(38)=2.660, p=0.011, Cohen's d=0.841).

Example 6. A Biomarker of Concussion

The preceding analyses validated the predictions that (1) children with a concussion have poorer neural processing of sound than their peers, (2) this profile is grounded in neural processing of the $F_0$, and (3) the integrity of this processing relates to the severity of the injury. Next, it was hypothesized that these physiological measures could be combined to classify children into concussion and control groups. If so, certain FFR properties could be used in aggregate as a biological marker to objectively and reliably identify a concussion.

A binary logistic regression was conducted, which asks how a series of measures combine to predict group membership. While the previous sections defined the specific neural functions that are disrupted in children with a concussion, how the FFR distinguishes between individuals with and without these injuries was evaluated in these experiments. A particular goal was to determine if these objective biological factors could, in combination, identify the children in this study who had sustained a concussion. A two-step model was used that, on the first step, incorporated subject age, the background noise in the FFR (amplitude of non-stimulus-related neural activity), and the timing of the onset response to sound (wave V in response to a click). The second step incorporated (singly and in various combinations) the amplitude of the response to the $F_0$, the size of the onset response (defined here as the area between Peaks V and A), the accuracy of encoding the speech sound (stimulus-response correlation), and response amplitude over the harmonic coding region (defined here as 175-750 Hz). When the second step of the model included amplitude of the response to the $F_0$, size of the onset response, and the stimulus-response correlation, the model correctly classified subjects into concussion or control groups as shown in Table 2 (Log likelihood ratio=23.028, Nagelkerke R2=0.741, $X^2(6)$=32.423, p<0.001). The percentage of subjects accurately classified varied depending upon response components selected for the second step.

TABLE 2

A binary logistic regression that incorporates multiple aspects of auditory-neurophysiological processing reliably classifies 90% of children into concussion or control groups.

|  |  | B | S.E. | Wald $\chi^2$ |
|---|---|---|---|---|
| Step 1 | Age | −0.24 | 0.33 | 0.52 |
|  | Prestimulus amplitude | −11.26 | 63.67 | 0.03 |
|  | Wave V ABR latency | 2.545 | 2.99 | 0.72 |
| Step 2 | CV onset amplitude | 40.14 | 17.54 | 5.33* |
|  | $F_0$ amplitude | −161.82 | 59.74 | 7.34* |
|  | Stimulus-response correlation | −20.83 | 8.63 | 5.82** |

*p < 0.05,
**p = 0.01.

Finally, the predictive utility of the model described in Table 2 was evaluated by conducting a receiver operating characteristic (ROC) analysis on scores from the logistic regression. A cut-off of 0.596 on the regression score was found to achieve a 90% sensitivity (true positive rate; 18 out of 20 mTBI subjects correctly classified) and a 95% specificity (true negative rate; 19 out of 20 control subjects correctly classified) was an excellent fit for the data (area under the curve=0.945, p<0.001, 95% confidence interval 0.875-1.000; see FIG. 10). These correspond to a 94.7% positive predictive value (PPV, probability that a positive is true) and a 90.4% negative predictive value (NPV, probability that a negative is true). For comparison, the ImPACT—a widely-used, behavioral test battery—has an 89.4$ PPV and 81.9% NPV.[11] Similarly, the Standardized Assessment of Concussions has a 91.2% PPV and an 83.1% NPV.[12]

Example 7. Partial Recovery of Neural Processing as Concussion Symptoms Abate

Figure 4A:
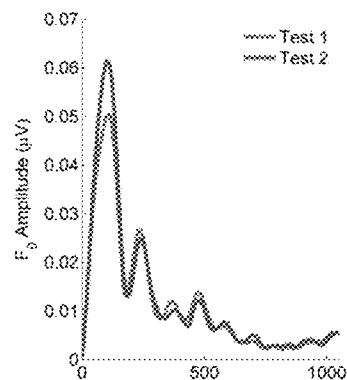
FIG. 4A-C depicts graphs showing the longitudinal evidence that $F_0$ processing improves as concussion symptoms abate. Between Test 1 and Test 2 (burgundy and red lines, respectively) the amplitude of responses to the $F_0$ increases (A). The mean (±1 S.E.M.) of the concussion group at both test points. On average, they no longer differ from the control group with respect to $F_0$ processing (mean±1 S.E.M. showed as gray shaded region) (B). Although 5 of the subjects are within this range, 6 show increases beyond that range. Changes in $F_0$ amplitude for individual subjects from the concussion group are shown (C). The shaded gray area shows the range $F_0$ amplitude that would indicate chance level of change based on normative data.
Figure 4B:
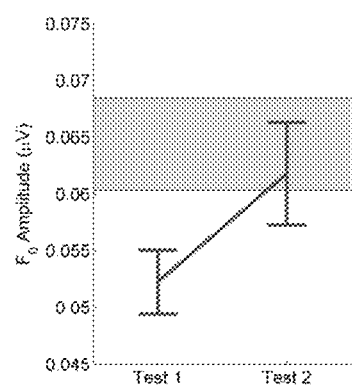
Figure 4C:
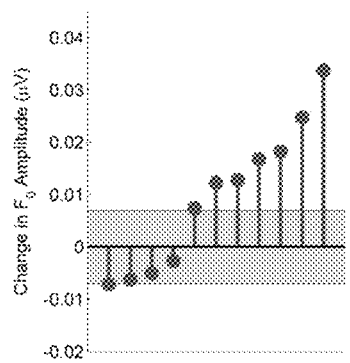

The final analysis focused on children who returned to the clinic for a second evaluation. If sound processing is disrupted by a concussion, then it follows that this processing should improve through the course of recovery. At the second test, all of the children reported a reduction in their symptom loads, suggesting that they were on the road to recovery (subgroup only; PCSS: Test 1, mean 37.1, SD 22.5; Test 2, mean 12.8, SD 15.2; t(10)=4.342, p=0.002). It is important to note, however, that only one of the children was clinically determined to be completely recovered from the concussion at this second visit and cleared to resume normal activities. In line with this reduction in symptom load, $F_0$ responses were found to be ~30% larger at the second test, whereas responses to the harmonics remained the same (test×frequency interaction, F(1, 10)=6.287, p=0.031, $\eta^2$=0.386; $F_0$: t(10)=2.397, p=0.037; harmonics: t(10)= 1.453, p=0.177). As illustrated in FIG. 4B, the re-test group's $F_0$ amplitude matched the range of the control group. The minimal detectable change in $F_0$ amplitude based on published norms[9] was also computed; this provides a cutoff for a change in $F_0$ amplitude that would be more than expected by chance[10]. 6 of the 11 children in this group improved in $F_0$ amplitude beyond chance (change of 0.006 μV). As shown in FIG. 4C, of the five that did not significantly increase in $F_0$ amplitude, none declined significantly. While this is a small subsample, this longitudinal evidence for $F_0$ recovery provides a converging proof-of-concept that reinforces the cross-sectional findings.

Example 8. Detection of Lasting Neurological Damage in Subjects With a Previous Non-Penetrating Brain Injury Twenty-five male student-athletes with a history of one concussion (11-82 months before participation; mean=36.1, SD=20.0) were recruited from a college football team. All were healthy and active at the time of testing. Controls were twenty-five age- and position-matched teammates who reported no previous concussions. Frequency-following responses (FFRs) to speech, an electrophysiological response from the auditory midbrain that depends on synchronous neural firing and reflects auditory pathway health with microsecond precision, provided our outcome measure. The approach used is substantially similar to methods outlined in Example 1.

Figure 5A:
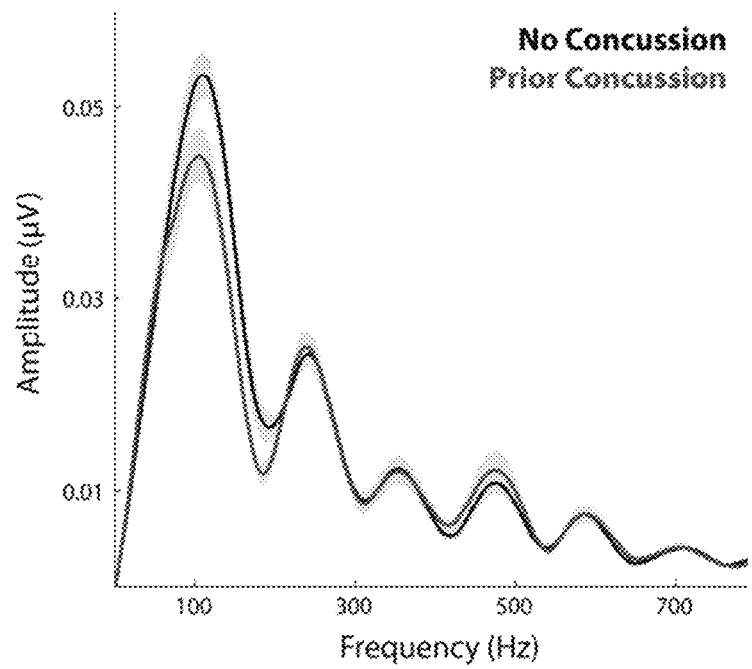
FIG. 5A-B show graphs depicting neural responses in the frequency domain. (A) Student-athletes with one prior concussion (blue) have smaller $F_0$ responses (at 100 Hz) than their teammates who have never had a concussion (black). The two groups have similar responses to the higher-frequency harmonics, however. (B) Percentiles are shown for $F_0$ responses referenced to published norms. Student-athletes, on average, perform around the $40^{th}$ percentile. Those with a previous concussion, however, perform around the $20^{th}$ percentile. Shaded regions and error bars indicate 1 SEM.

Student-athletes with and without a previous concussion responded distinctly to the $F_0$ and harmonics (FIG. 5A; group×frequency interaction: F(1,48)=6.012, p=0.018, $\eta^2$=0.111). Student-athletes with one previous concussion had smaller F0 responses than those without (t(48)=2.251, p=0.029, Cohen's d=0.918; Concussion mean (SD)=0.0467 μV (0.0014), 95% CI=[0.0407, 0.0527]; No Concussion mean (SD)=0.0557 μV (0.0138), 95% CI=[0.0500, 0.0613]). These groups had similar responses to harmonics (t(48)= 0.066, p=0.947, Cohen's d=0.021; Concussion mean (SD)= 0.0155 μV (0.0060), 95% CI=[0.013, 0.018]; No concussion mean (SD)=0.0154 μV (0.0031), 95% CI=[0.013, 0.017]).

Figure 5B:
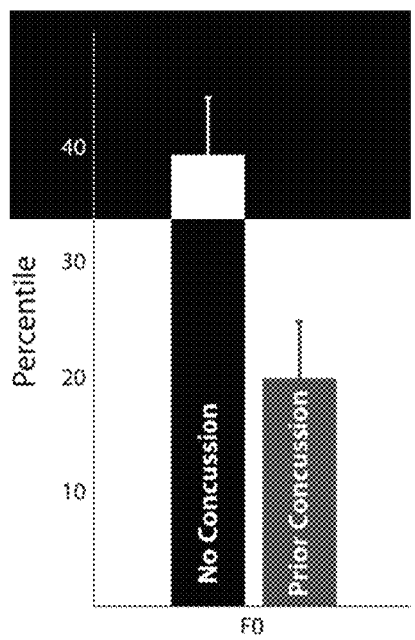

As a whole, the student-athletes had $F_0$ responses below the $50^{th}$ percentile for this age group[9] (FIG. 5B; one-sample t-test: t(49)=4.507, p<0.001, mean percentile=28.4, 95% CI=[20.6, 37.8]). On average, the group without a previous concussion had $F_0$s at the $38.5^{th}$ percentile (t(24)=1.837, p=0.079, 95% CI=[25.6, 51.4]) whereas the group with a previous concussion had $F_0$s at the $19.8^{th}$ percentile (t(24)= 4.628, p<0.001, 95% CI=[11.0, 31.9]).

Overall, student-athletes with a prior concussion had smaller responses to the $F_0$ of speech than their teammates who never experienced a concussion. The putative legacy of this injury was evident despite indications that student-athletes had recovered. This neural hallmark of a previous concussion manifests similarly—albeit more mildly—as that observed in younger, symptomatic concussed student-athletes.

REFERENCES FOR THE EXAMPLES

1. Gallun, F. J. et al. Performance on tests of central auditory processing by individuals exposed to high-intensity blasts. *J. Rehabil. Res. Dev.* 49, 1005 (2012).
2. Skoe, E. & Kraus, N. Auditory brain stem response to complex sounds: A tutorial. *Ear Hear.* 31, 302-324 (2010).

3. Skoe, E., Krizman, J., Anderson, S. & Kraus, N. Stability and plasticity of auditory brainstem function across the lifespan. *Cereb. Cortex* 25, 1415-1426 (2015).
4. Kraus, N. & Nicol, T. Brainstem origins for cortical 'what' and 'where' pathways in the auditory system. *Trends Neurosci.* 28, 176-181 (2005).
5. Carcagno, S. & Plack, C. J. Subcortical plasticity following perceptual learning in a pitch discrimination task. *JARO-J. Assoc. Res. Otolaryngol.* 12, 89-100 (2011).
6. McCrory, P. et al. Consensus statement on concussion in sport: the 4th International Conference on Concussion in Sport held in Zurich, November 2012. *Br. J. Sports Med.* 47, 250-258 (2013).
7. Kontos, A. P. et al. A revised factor structure for the Post-Concussion Symptom Scale baseline and postconcussion factors. *Am. J. Sports Med.* 40, 2375-2384 (2012).
8. Joyce, A. S., LaBella, C. R., Carl, R. L., Lai, J.-S. & Zelko, F. A. The Postconcussion Symptom Scale: Utility of a three-factor structure. *Med. Sci. Sports Exerc.* 47, 1119-1123 (2015).
9. Skoe E, Krizman J, Anderson S, Kraus N. Stability and plasticity of auditory brainstem function across the lifespan. *Cereb Cortex.* 25, 1415-1426 (2015).
10. Vander Roer et al. Minimal clinically important change for pain intensity, functional status, and general health status in patients with nonspecific low back pain. *Spine* 31: 578-582 (2006).
11. Schartz et al. *Arch. Clin. Neuropsychol.* 21, 91-99 (2006).
12. Barr et al. *J. Int. Neuropsychol. Soc.* 7, 693-702 (2001).

The invention claimed is:

1. A method of identifying non-penetrating brain injury in a subject, the method comprising:
    (a) administering to the subject an acoustic stimulus, wherein the acoustic stimulus is comprised of a complex sound, and the complex sound comprises a consonant, a consonant-to-vowel transition, and optionally a vowel;
    (b) recording using electrodes fitted to the subject, voltage potentials from the subject's brain for at least the duration of the acoustic stimulus;
    (c) analyzing the voltage potentials to determine one or more components of the subject's brain response to the acoustic stimulus; and
    (d) generating an indication of non-penetrating brain injury in the subject by identifying the subject as having a non-penetrating brain injury when a value for at least one component of the brain response to the acoustic stimulus is anomalous;
    wherein the components are selected from the group consisting of fundamental frequency ($F_0$), neural timing of a sustained response peak, response amplitude over a time window that comprises some or all of the consonant-to-vowel transition, and stimulus-response correlation over a time window that encompasses some or all of the consonant-to-vowel transition.

2. A method of identifying non-penetrating brain injury in a subject, the method comprising:
    (a) analyzing one or more components of the subject's brain response to an acoustic stimulus, wherein the acoustic stimulus is comprised of a complex sound, and the complex sound comprises a consonant, a consonant-to-vowel transition, and optionally a vowel; and
    (b) generating an indication of non-penetrating brain injury in the subject by identifying the subject as having a non-penetrating brain injury when a value for at least one component of the brain response is anomalous,
    wherein the components are selected from the group consisting of fundamental frequency ($F_0$), neural timing of a sustained response peak, response amplitude over a time window that comprises some or all of the consonant-to-vowel transition, and stimulus-response correlation over a time window that encompasses some or all of the consonant-to-vowel transition.

3. A method for classifying a subject that received a hit to the body that transmitted an impulsive force to the brain, the method comprising:
    (a) administering to the subject an acoustic stimulus, wherein the acoustic stimulus is comprised of a complex sound, and the complex sound comprises a consonant, a consonant-to-vowel transition, and optionally a vowel;
    (b) recording with electrodes fitted to the subject, voltage potentials from the subject's brain for at least the duration of the acoustic stimulus;
    (c) analyzing the voltage potentials to determine one or more components of the brain response; and
    (d) generating an indication that the subject received a hit to the body that transmitted an impulsive force to the brain by classifying the subject as having a non-penetrating brain injury when a value for at least one component of the brain response is anomalous;
    wherein the components are selected from the group consisting of fundamental frequency ($F_0$), neural timing of a sustained response peak, response amplitude over a time window that comprises some or all of a consonant-to-vowel transition, and stimulus-response correlation over a time window that encompasses some or all of a consonant-to-vowel transition.

4. A method for classifying a subject that received a hit to the body that transmitted an impulsive force to the brain, the method comprising:
    (a) analyzing one or more components of the subject's brain response to an acoustic stimulus, wherein the acoustic stimulus is comprised of a complex sound, and the complex sound comprises a consonant, a consonant-to-vowel transition, and optionally a vowel; and
    (b) generating an indication that the subject received a hit to the body that transmitted an impulsive force to the brain by classifying the subject as having a non-penetrating brain injury when a value for at least one component of the brain response is anomalous,
    wherein the component(s) is selected from the group consisting of fundamental frequency ($F_0$), neural timing of a sustained response peak, response amplitude over the consonant-to-vowel transition, and stimulus-response correlation over a time window that encompasses the consonant-to-vowel transition.

5. The method of claim 1, wherein the subject is asymptomatic.

6. The method of claim 1, wherein the subject is symptomatic.

7. A method for assessing a subject's recovery from a non-penetrating brain injury, the method comprising:
    (a) testing the subject's brain response to an acoustic stimulus by:
        (i) administering to the subject an acoustic stimulus, wherein the acoustic stimulus is comprised of a complex sound, and the complex sound comprises a consonant, a consonant-to-vowel transition, and optionally a vowel;

(ii) recording using electrodes fitted to the subject, voltage potentials from the subject's brain for at least the duration of the acoustic stimulus;

(iii) analyzing the voltage potentials to determine one or more components of the subject's brain response to the acoustic stimulus; and (iv) identifying a value for at least one component of the brain response that is anomalous;

wherein the components are selected from the group consisting of fundamental frequency ($F_0$), neural timing of a sustained response peak, response amplitude over a time window that comprises some or all of the consonant-to-vowel transition, and stimulus-response correlation over a time window that encompasses some or all of the consonant-to-vowel transition;

(b) re-testing the subject's brain response to the acoustic stimulus at a later time by repeating steps a(i) to a(iii), and identifying the value for the one or more components that were anomalous in step (a)(iv) ("the re-test value"); and (c) calculating the difference between the re-test value and the anomalous value;

wherein the subject is determined to be recovering from the non-penetrating brain injury when there is a change in the re-test value that is greater than would be expected by chance, and a direction of the change indicates an improvement in the component of the brain response; and wherein the subject is determined to not be recovering from the non-penetrating brain injury when (a) there is not a change in the re-test value that is greater than would be expected by chance, and the direction of the change indicates an improvement in the component of the brain response, or (b) when there is a change in the re-test value that is greater than would be expected by chance, and the direction of the change indicates a deterioration in the component of the brain response.

8. The method of claim 7, wherein the subject is symptomatic at the time of testing.

9. The method of claim 8, wherein the subject reports an improvement in symptoms at re-testing.

10. The method of claim 8, wherein the subject reports no improvement in symptoms at re-testing.

11. The method of claim 7, wherein the subject is asymptomatic at the time of testing.

12. The method of claim 1, wherein at least one component of the brain response comprises $F_0$ and the value is $F_0$ amplitude, $F_0$ phase consistency, $F_0$ sharpness, $F_0$ frequency error, pitch tracking, or any combination thereof.

13. The method of claim 12, wherein at least one component of the brain response comprises $F_0$ amplitude.

14. The method of claim 1, wherein at least one component of the brain response comprises neural timing of a sustained response peak.

15. The method of claim 1, wherein at least one component of the brain response comprises response amplitude over a time window that comprises some or all of a consonant-vowel transition.

16. The method of claim 1, wherein at least one component of the brain response comprises stimulus-response correlation over a time window that comprises some or all of a consonant-vowel transition, and the stimulus-response correlation is calculated in the time domain.

17. The method of claim 1, wherein at least one component of the brain response comprises stimulus-response correlation over a time window that comprises some or all of a consonant-vowel transition, and the stimulus-response correlation is calculated in the frequency domain.

18. The method of any one of claims 15 to 17, wherein the time window comprises at least one formant.

19. The method of any one of claims 15 to 17, wherein the time window comprises at least two formants.

20. The method of any one of claims 15 to 17, wherein the time window further comprises the unvoiced consonant release and/or the transient frequency following response component corresponding to the onset of voicing.

21. The method of claim 1, wherein the subject is identified as having a non-penetrating brain injury when values for at least two components are anomalous.

22. The method of claim 1, wherein the subject is identified as having a non-penetrating brain injury when values for at least three components are anomalous.

23. The method of claim 1, wherein a value for at least one component of the brain response is a measurement produced by a statistical model, the statistical model comprising a value for a component selected from the group consisting of fundamental frequency ($F_0$), neural timing of a sustained response peak, response amplitude over a time window that comprises some or all of the consonant-vowel transition, and stimulus-response correlation over a time window that encompasses some or all of the consonant-vowel transition.

24. The method of claim 23, wherein the statistical model comprises two or more values, each value for a component selected from the group consisting of fundamental frequency ($F_0$), neural timing of a sustained response peak, response amplitude over a time window that comprises some or all of the consonant-vowel transition, and stimulus-response correlation over a time window that encompasses some or all of the consonant-vowel transition.

25. The method of any one of claims 21 to 24, wherein the two components are $F_0$ and stimulus-response correlation over a time window that encompasses the consonant-vowel transition.

26. The method of claim 1, wherein at least one component of the brain response further comprises onset peak amplitude or onset response amplitude.

27. The method of claim 1, wherein the acoustic stimulus further comprises a background noise.

28. The method of claim 1, wherein the acoustic stimulus is repeatedly administered to the subject; voltage potentials are recorded for at least the duration of the repeated acoustic stimuli; and an average response to the acoustic stimulus is produced from the recorded voltage potentials before determining one or more components of the FFR.

29. The method of claim 1, wherein the consonant is an obstruent stop consonant.

30. The method of claim 1, wherein the vowel is a low, back vowel.

31. The method of claim 1, wherein the complex sound comprises a speech syllable selected from the group consisting of /da/, /pa/, /ka/, /ta/, /ba/, and/ga/.

32. The method of claim 1, wherein the complex sound comprises a speech syllable selected from the group consisting of /da/, /pa/, /ka/, /ta/, /ba/, and/ga/, with the provisio that the complex sound is not a word.

33. The method of claim 1, wherein the complex sound consists of a speech syllable selected from the group consisting of /da/, /pa/, /ka/, /ta/, /ba/, and/ga/.

* * * * *